(12) United States Patent
Naito et al.

(10) Patent No.: US 12,023,125 B2
(45) Date of Patent: Jul. 2, 2024

(54) MEASUREMENT DEVICE FOR LIVING TISSUE, SUCTION DEVICE, MEASUREMENT METHOD FOR LIVING TISSUE, AND PROGRAM

(71) Applicant: Japan Tobacco Inc., Tokyo (JP)

(72) Inventors: Hirotaka Naito, Tokyo (JP); Yuta Yoshimura, Tokyo (JP); Hiroyuki Kubota, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 18/071,374

(22) Filed: Nov. 29, 2022

(65) Prior Publication Data

US 2023/0086075 A1    Mar. 23, 2023

Related U.S. Application Data

(63) Continuation of application No. PCT/JP2020/041022, filed on Nov. 2, 2020.

(51) Int. Cl.
*A61B 5/00*    (2006.01)
*G01N 21/17*    (2006.01)

(52) U.S. Cl.
CPC .............. *A61B 5/00* (2013.01); *G01N 21/17* (2013.01)

(58) Field of Classification Search
CPC ........... A61B 5/00; A61B 5/0059; A61B 5/01; A61B 5/4552; A61B 5/682;
(Continued)

(56) References Cited

U.S. PATENT DOCUMENTS 11,150,332 B1 *  10/2021  Chen ....................... G01S 17/08
2006/0183982 A1   8/2006  Shioi
(Continued)

FOREIGN PATENT DOCUMENTS

CN    109007975 A    12/2018
JP    2006-81893 A    3/2006
(Continued)

OTHER PUBLICATIONS

International Search Report for PCT/JP2020/041022 (PCT/ISA/210) dated Jan. 19, 2021.
(Continued)

*Primary Examiner* — Thanh Luu
*Assistant Examiner* — Monica T Taba
(74) *Attorney, Agent, or Firm* — Birch, Stewart, Kolasch & Birch, LLP

(57) ABSTRACT

The present disclosure provides a measuring device for biological tissue by using an optical sensor, the device being compact enough to fit in a user's hand and casually usable by the user. The measuring device is provided with: an optical sensor that measures optical data about an object of measurement through a measurement surface in contact with the object of measurement by irradiating the object of measurement with light from a light emitter and causing a light receiver to receive reflected light that is reflected from the object of measurement, the object of measurement being a portion of biological tissue; a temperature sensor that measures the temperature of the optical sensor; and a data processor that processes the optical data on the basis of the temperature of the optical sensor and derives a measurement result pertaining to the object of measurement on the basis of the processed optical data.

18 Claims, 17 Drawing Sheets

(58) Field of Classification Search
CPC .............. A61B 5/14507; A61B 5/0088; A61B 5/14517; A61B 5/1455; A61B 5/443; A61B 5/4542; A61B 5/6898; A61B 2560/0252; G01N 21/17; G01N 21/3554; G01N 2201/1211; G01N 21/359; G01N 21/474

See application file for complete search history.

(56) References Cited

U.S. PATENT DOCUMENTS

| | | | | |
|---|---|---|---|---|
| 2007/0023034 | A1* | 2/2007 | Jongejan | A61M 15/009 128/200.14 |
| 2007/0047603 | A1* | 3/2007 | Oomori | H04B 10/572 372/38.07 |
| 2008/0309939 | A1 | 12/2008 | Sugawara | |
| 2018/0140016 | A1 | 5/2018 | Thorens | |
| 2018/0146708 | A1 | 5/2018 | Batista | |
| 2018/0161531 | A1* | 6/2018 | Costella | A61M 15/0021 |
| 2018/0328835 | A1* | 11/2018 | Bauer | A61B 5/6843 |
| 2021/0370089 | A1* | 12/2021 | Anash | A61K 47/46 |

FOREIGN PATENT DOCUMENTS

| | | |
|---|---|---|
| JP | 2007-127666 A | 5/2007 |
| JP | 2018-523982 A | 8/2018 |
| JP | 2018-526971 A | 9/2018 |
| JP | 2019-507319 A | 3/2019 |
| JP | 2020-68739 A | 5/2020 |
| RU | 2 081 405 C1 | 8/1996 |
| WO | WO 2005/092192 A1 | 10/2005 |
| WO | WO 2007/116675 A1 | 10/2007 |
| WO | WO 2019/173923 A1 | 9/2019 |

OTHER PUBLICATIONS

Russian Office Action for corresponding Russian Application No. 2022128175, dated Nov. 27, 2023, with English translation.

Timanin, "Mechanical Impedance of Biological Tissues in a Model with Preset Displacements on the Surface of a Hall-Space," Acoustic Journal, vol. 53, No. 5, 2007, pp. 724-727, with English abstract.

* cited by examiner

MEASUREMENT DEVICE FOR LIVING TISSUE, SUCTION DEVICE, MEASUREMENT METHOD FOR LIVING TISSUE, AND PROGRAM

CROSS REFERENCE TO RELATED APPLICATION

This application is a Continuation of PCT International Application No. PCT/JP2020/041022, filed on Nov. 2, 2020, which is hereby expressly incorporated by reference into the present application.

TECHNICAL FIELD

The present disclosure relates to a measuring device for biological tissue, an inhalation device, a measuring method for biological tissue, and a program.

BACKGROUND ART

A measuring device for measuring the amount of a substance in biological tissue such as moisture inside the oral cavity is known. In such a measuring device, various sensors for measuring biological tissue are adopted. One example of a sensor applied to a measuring device for biological tissue is a sensor (optical sensor) using an optical element.

On the other hand, the application of a measuring mechanism for measuring the amount of a substance in biological tissue to a smoking implement such as a smoking device carried by the user is also known. A smoking device provided with a measuring device for measuring the amount of a substance in biological tissue is also an example of a measuring device for biological tissue. By adopting an electrochemical sensor in such a smoking device, for example, the quantity and concentration of nicotine metabolites in the saliva of a user who is a smoker are measured.

CITATION LIST

Patent Literature

PTL 1: International Publication No. WO 2005/092192
PTL 2: Japanese Patent Laid-Open No. 2007-127666
PTL 3: International Publication No. WO 2007/116675
PTL 4: Japanese Translation of PCT International Application Publication No. 2018-526971
PTL 5: Japanese Translation of PCT International Application Publication No. 2018-523982
PTL 6: International Publication No. WO 2019/173923

SUMMARY OF INVENTION

Technical Problem

A measuring device adopting an optical sensor is largely influenced by temperature when heat is produced, and to accommodate an adequate heat radiation mechanism, the measuring device is typically a bulky device like those used in laboratories and factories. Moreover, since it takes time for an optical sensor to stabilize operations after being started up, the measurement time is usually long. In other words, a device which adopts an optical sensor for measuring biological tissue and which can be used casually by a user has not been available. Furthermore, in the case where a measuring mechanism is applied to a smoking implement, heating is also expected to occur when generating a smokable component, which necessitates particular consideration regarding how the optical sensor is influenced by heating.

One objective of the present disclosure is to provide a measuring device for biological tissue by using an optical sensor, the device being compact enough to fit in a user's hand and casually usable by the user. Another objective of the present disclosure is to provide a measuring device in which the measurement accuracy of the amount of a substance in biological tissue is improved by appropriately processing optical data acquired by an optical sensor. Furthermore, another objective of the present disclosure is to apply such a measuring mechanism using an optical sensor to an inhalation device such as a smoking implement.

Solution to Problem

In a first aspect, a measuring device for biological tissue is provided. The measuring device is provided with: an optical sensor that measures optical data about an object of measurement through a measurement surface in contact with the object of measurement by irradiating the object of measurement with light from a light emitter and causing a light receiver to receive reflected light that is reflected from the object of measurement, the object of measurement being a portion of biological tissue; a temperature sensor that measures the temperature of the optical sensor; and a data processor that processes the optical data on the basis of the temperature of the optical sensor and derives a measurement result pertaining to the object of measurement on the basis of the processed optical data.

According to a measuring device of a second aspect, in the measuring device of the first aspect, the processing of the optical data by the data processor includes selecting the optical data for which the temperature of the optical sensor substantially corresponds to a designated temperature.

According to a measuring device of a third aspect, in the measuring device of the second aspect, the designated temperature is determined dynamically on the basis of the ambient temperature when the measuring device is started up.

According to a measuring device of a fourth aspect, in the measuring device of any of the first to third aspects, the processing of the optical data by the data processor includes correcting the optical data for each wavelength of the reflected light on the basis of the temperature of the optical sensor.

According to a measuring device of a fifth aspect, in the measuring device of the fourth aspect, a model of the rate of change of light intensity with respect to the temperature of the optical sensor is defined for each wavelength in advance and stored in storage, and the optical data is corrected by using the model.

According to a measuring device of a sixth aspect, in the measuring device of any of the first to fifth aspects, the light emitter is activated if the temperature of the optical sensor is equal to or lower than a prescribed threshold value, and the light emitter is deactivated if the temperature of the optical sensor is higher than the prescribed threshold value.

According to a measuring device of a seventh aspect, in the measuring device of any of the first to sixth aspects, the measurement surface is provided with an optically transparent window.

According to a measuring device of an eighth aspect, in the measuring device of the seventh aspect, the measurement surface is disposed on an inclined surface at a position between the light receiver and the light emitter.

According to a measuring device of a ninth aspect, in the measuring device of the eighth aspect, the angle of inclination of the inclined surface is less than or equal to 15 degrees.

According to a measuring device of a 10th aspect, in the measuring device of any of the first to sixth aspects, the light emitter and the light receiver are joined to the measurement surface through an optical fiber.

According to a measuring device of an 11th aspect, in the measuring device of the 10th aspect, the optical fiber is provided with a first fiber joining the light emitter and the measurement surface and a second fiber joining the light receiver and the measurement surface, and the distance between the end of the first fiber on the measurement surface side and the end of the second fiber on the measurement surface side is within a range from 0 mm to 3 mm.

According to a measuring device of a 12th aspect, in the measuring device of any of the 1st to 11th aspects, the measuring device is provided to an inhalation device and is integrated with the inhalation device.

According to a measuring device of a 13th aspect, in the measuring device of the 12th aspect, the temperature sensor is disposed between an air channel provided in the inhalation device and the optical sensor.

According to a measuring device of a 14th aspect, in the measuring device of any of the 1st to 11th aspects, the measuring device is removably attached to an inhalation device.

According to a measuring device of a 15th aspect, in the measuring device of any of the 12th to 14th aspects, the object of measurement is oral tissue.

In a 16th aspect, an inhalation device provided with the measuring device of any of the 1st to 15th aspects is provided.

In a 17th aspect, a measuring method for biological tissue is provided. The measuring method includes: a step of a temperature sensor measuring the temperature of an optical sensor; a step of the optical sensor measuring optical data, the step including irradiating an object of measurement with light and receiving reflected light that is reflected from the object of measurement through a measurement surface in contact with the object of measurement, the object of measurement being a portion of biological tissue; a step for processing the optical data on the basis of the temperature of the optical sensor; and a step for deriving a measurement result pertaining to the object of measurement on the basis of the processed optical data.

According to a method of an 18th aspect, in the measuring method of the 17th aspect, the step for processing the optical data includes selecting the optical data for which the temperature of the optical sensor substantially corresponds to a designated temperature.

According to a method of a 19th aspect, in the measuring method of the 17th or 18th aspect, the step for processing the optical data includes correcting the optical data for each wavelength of the reflected light on a basis of the temperature of the optical sensor.

In a 20th aspect, a program causing a measuring device to execute the measuring method of any of the 17th to 19th aspects is provided.

DESCRIPTION OF EMBODIMENTS

Figure 1:
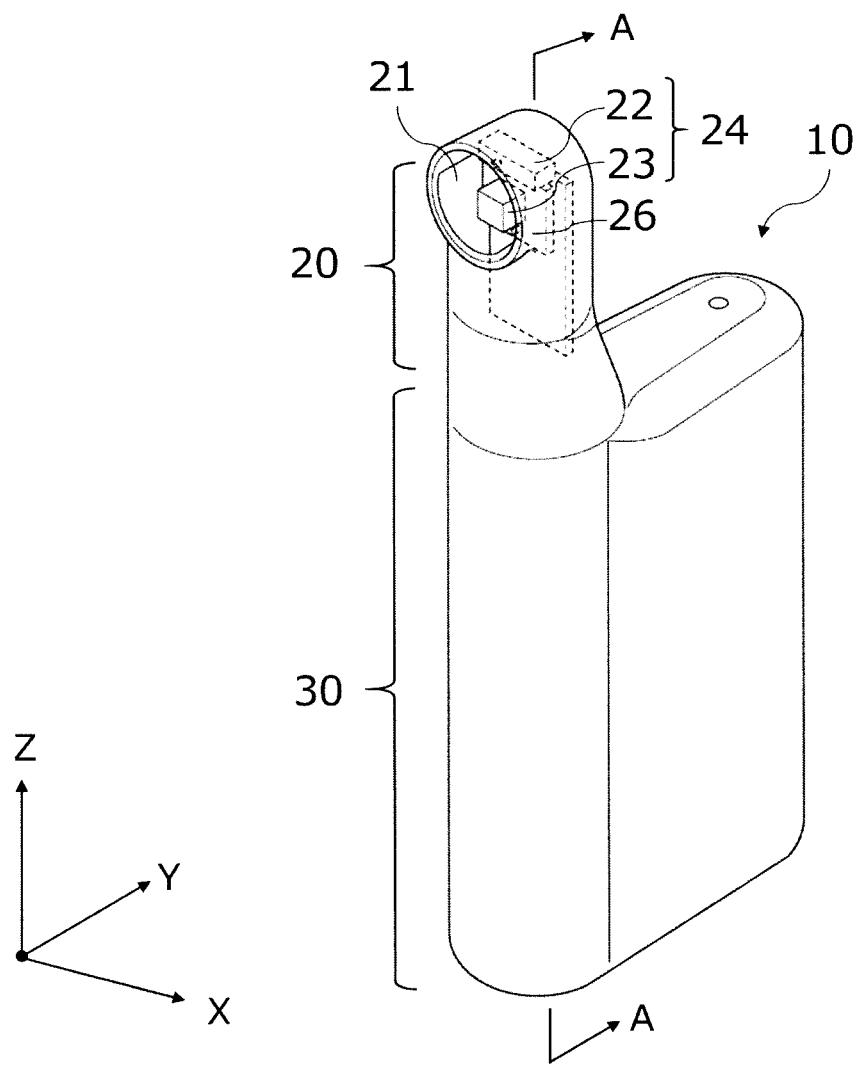
FIG. 1 is an overall perspective view of a measuring device for biological tissue according to an embodiment.

Hereinafter, an inhalation device according to an embodiment of the present disclosure will be described with reference to the accompanying drawings. In the accompanying drawings, the same or similar elements are denoted with the same or similar reference signs, and duplicate descriptions of the same or similar elements may be omitted from the description of each embodiment. Also, the features indicated in each embodiment are also applicable to other embodiments insofar as the embodiments do contradict each other. Furthermore, the drawings are schematic and do not necessarily correspond to actual dimensions, proportions, and the like. The drawings may also include portions where the dimensional relationships and ratios differ from each other.

A measuring device for biological tissue according to the present embodiment is a device which utilizes an optical sensor and which is compact enough to fit in a user's hand. In other words, the optical sensor can be utilized to take measurements by irradiating biological tissue with light. Such an optical sensor is provided with a light receiver and a light emitter. Additionally, by putting the measuring device in contact with an object of measurement, namely a portion of biological tissue, causing the light emitter to emit light, and causing the light receiver to receive reflected light that is reflected from the object of measurement, optical data about the object of measurement is measured.

In general, optical sensors are highly robust and the measuring element (optical element) is not exposed. Usability is also high because a film or the like for protecting the element is unnecessary. Furthermore, since it is not necessary to put the optical element in direct contact with biological tissue, the user is not made to feel uncomfortable.

On the other hand, a measuring device which uses an optical sensor and which is compact enough to fit in the user's hand is susceptible to noise due to heat produced when a light-emitting element emits light. Specifically, if the light-emitting element produces heat and the temperature of light-emitting element rises, the peak wavelength emitted thereafter increases. As a consequence, the light intensity of the reflected light received by a light-receiving element is lowered relatively. Moreover, since the user carries the compact measuring device, the measuring device is expected to be used in various seasons, indoors and outdoors. That is, the measuring device is readily influenced by temperature changes in the external environment. Due to these temperature-related factors, the measurement data varies greatly and the measurement accuracy of the measuring device is expected to be adversely impacted.

Accordingly, a measuring device for biological tissue according to the present embodiment is further provided with a temperature sensor that measures the temperature of the optical sensor, in addition to the configuration of the optical sensor described above. Furthermore, temperature information about the optical sensor and optical data are associated. More specifically, optical data acquired by the optical sensor is processed appropriately on the basis of the temperature of the optical sensor acquired by the temperature sensor, and a measurement result regarding biological tissue is derived on the basis of the processed optical data. With this configuration, an appropriate measurement result can be derived while also considering the impact of noise due to heat produced when the light-emitting element emits light, even in a compact measuring device.

Herein, the object of measurement to be measured by the measuring device for biological tissue may be anything measurable by the optical sensor. Note that the optical sensor can measure a plurality of wavelengths, and therefore the amounts of a variety of substances in biological tissue can be measured at the same time. Biological tissue includes the oral cavity, the skin on the surface of the body, and the like. In the case where the object of measurement is the oral cavity, a measurement result is derived by analyzing substances (such as moisture and glucose) in saliva, the physical properties of oral tissue (for example, the color of oral tissue and the degree of tongue roughness), and the like. Also, examples in the case where the object of measurement is the skin on the surface of the body include substances (such as moisture) in sweat, the physical properties of the skin (such as the dryness of the skin), and the like. The measuring device may also be applied to the measurement of the amount and physical properties of a substance not in biological tissue.

(1) First Embodiment (1-1) Overall Configuration Example of Measuring Device

Figure 2A:
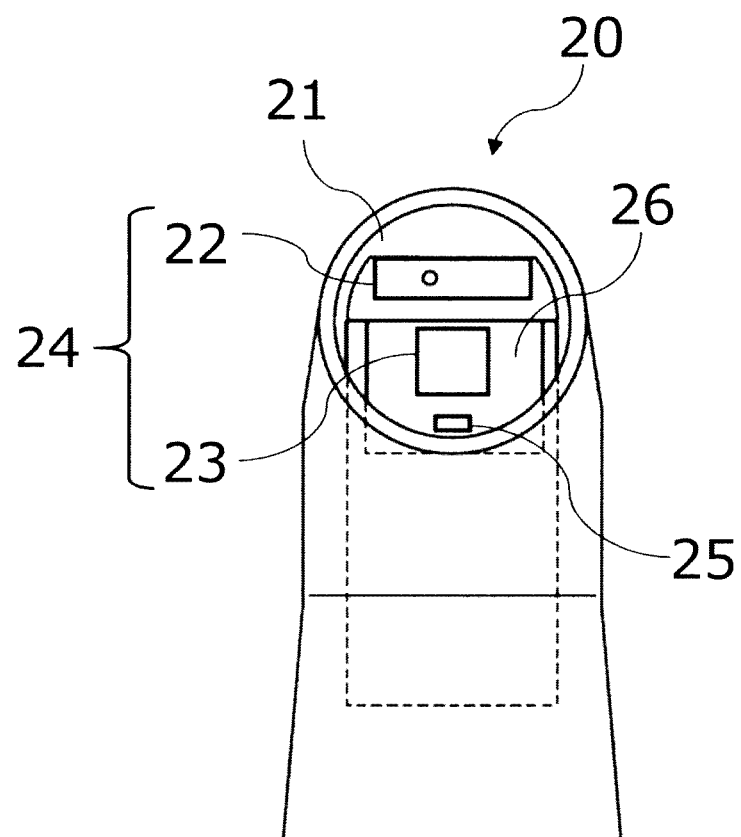
FIG. 2A is a plan view from the front of a measurer in the measuring device in FIG. 1.
Figure 2A:
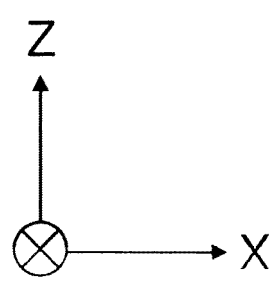
Figure 2B:
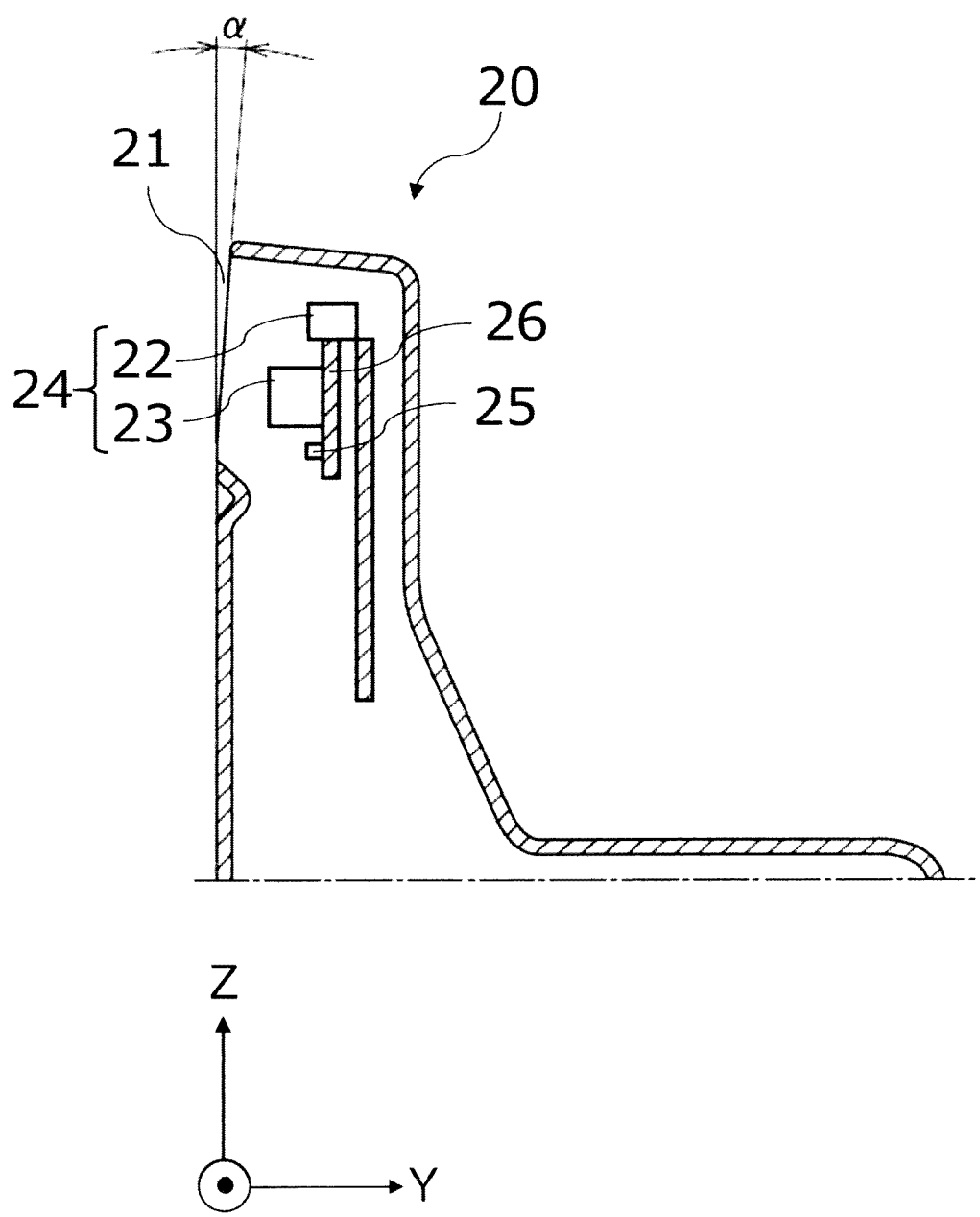
FIG. 2B is a cross section from the side of the measurer in the measuring device in FIG. 1.

FIG. 1 is an overall perspective view of a measuring device 10 for biological tissue according to an embodiment. Also, FIGS. 2A and 2B are schematic diagrams of a measurer 20 included in the measuring device 10. Specifically, FIG. 2A is a plan view from the front of the measurer 20 and FIG. 2B is a cross section illustrating a side view of the measurer 20, the cross section taken along the line A-A in FIG. 1.

For convenience, an X-Y-Z orthogonal coordinate system is defined in FIGS. 1, 2A, and 2B. That is, the Z axis points vertically upward, the X-Y plane cuts the measuring device 10 horizontally, and the Y axis points in the direction extending from the front surface to the back surface of the measuring device 10. Hereinafter, the X-Y-Z coordinate system illustrated in the drawings will be used in this sense.

The measuring device 10 is a device compact enough to fit in a user's hand. The measuring device 10 is provided with the measurer 20 for taking a measurement by being put into contact with biological tissue, and a main body 30. The measurer 20 is disposed so as to extend in the Z-axis direction from the upper surface of the main body 30. In addition, the measurer 20 forms a measurement surface 21 in the X-Z plane. That is, the user puts the object of measurement, namely a portion of biological tissue, in contact with the measurement surface 21, and thereby causes the biological tissue to be measured. Note that the measurement surface 21 may have an opening.

Internally, the measurer 20 is provided with: an optical sensor 24 including a light receiver 22 and a light emitter 23; a temperature sensor 25; and a heat radiator 26.

In the optical sensor 24, the light receiver 22 and the light emitter 23 are disposed in close proximity. More specifically, the light receiver 22 and the light emitter 23 are disposed closely with the light receiver 22 positioned above and the light emitter 23 positioned below in the vertical direction (+Z direction), and each element of the light receiver 22 and the light emitter 23 point in the –Y direction. Additionally, through the measurer 20, the light emitter 23 is configured to irradiate the object of measurement with light and the light receiver 22 is configured to receive reflected light reflecting from the object of measurement. For example, in the case where the object of measurement is the oral cavity, light emitted from the light emitter 23 irradiates the tongue inside the oral cavity and the lips, and the light receiver 22 receives the reflected light therefrom. With this arrangement, optical data about the object of measurement is measured. Note that the light receiver 22 and the light emitter 23 are not limited to the above-described positional relationship, and may also be positioned with the light receiver 22 below and the light emitter 23 above in the +Z direction. Also, the optical data may include, but is not limited to, a plurality of light wavelength data and the light intensity on each wavelength.

The light receiver 22 of the optical sensor 24 is provided with a light-receiving element. In the example in FIGS. 1, 2A, and 2B, a photodiode (PD) is adopted as the light-receiving element to achieve a compact measuring device 10. However, the light receiver 22 is not limited thereto, and a phototube or a photomultiplier tube using the external photoelectric effect (photoelectron emission), a phototransistor, an avalanche photodiode, a photoconductive cell, an image sensor, or a photocell using the internal photoelectric effect of a semiconductor, a radiation thermocouple or a thermopile that detects heat due to light absorption, a pyroelectric detector utilizing the pyroelectric effect, or the like may also be adopted.

Additionally, the light receiver 22 of the optical sensor 24 may also be provided with a wavelength specifier (not illustrated) such as a spectral element or an optical filter that receives one or more specific wavelengths. The spectral element may be, but is not limited to, a diffraction grating, a prism, or the like having a wavelength-selective mechanism. With this arrangement, multiple types of biological information can be acquired as optical data pertaining to a plurality of wavelengths. That is, the amounts of a plurality of substances in biological tissue can be measured at the same time. The wavelength specifier may be integrated with the light-receiving element.

The light emitter 23 of the optical sensor 24 is provided with a light-emitting element. The light emitter 23 may be, but is not limited to, a thermal radiation light source, a thermoluminescence light source, an electroluminescence light source, a laser, or the like. In the example in FIGS. 1, 2A, and 2B, a light-emitting diode (LED) is adopted as the light-emitting element to achieve a compact measuring device 10. However, the light-emitting element is not limited to the above, and a laser diode (LD), a fluorescent lamp, or an incandescent lamp may also be adopted. In particular, to measure a variety of substances in biological tissue, a wideband LED may be adopted as the light-emitting element in the measuring device 10.

Note that for the light receiver 22 to efficiently receive light which is emitted from the light emitter 23 and reflected from the object of measurement, an inclined surface may be formed by inclining the measurement surface 21 by an angle α toward the light receiver 22 (in the case of FIG. 2B, the +Y direction) with respect to the vertical direction (+Z direction). Note that the direction of the incline is such that, in FIG. 2B, the angle of incidence from the light emitter 23 to the measurement surface 21 is small compared to the case of no gradient with respect to the +Z direction. The measurement surface 21 is inclined in this way for the following reason.

Light emitted from the LED which may be adopted as the light emitter 23 travels straight ahead while spreading out in all directions. In particular, a person skilled in the art knows that for an angle of radiation in the range from 0° to 60°, an intensity of 50% or higher compared to light traveling straight ahead is maintained. A person skilled in the art also knows that if a mechanism such as an optical filter having a slit is adopted as the light receiver 22, the angle at which reflected light is incident on the light receiver 22 influences the received light intensity. In contrast, as a result of thorough investigation, the inventor obtained the finding that by inclining the measurement surface 21 by a prescribed angle toward the light receiver 22, the angle of incidence on the light receiver 22 can be reduced and the light reception sensitivity can be improved compared to the case of no incline. In particular, in the measuring device 10 of one embodiment, the inclination angle α may be adjusted in the range from 0° to 15°, more preferably adjusted in the range from 1° to 5° (for example, 2°). Note that a person skilled in the art understands that if the positional relationship of the light receiver 22 and the light emitter 23 in FIG. 2B is transposed, the direction of the incline is reversed (that is, inclined –α degrees with respect to the +Z direction).

The temperature sensor 25 measures the temperature of the optical sensor 24. As described above, heat produced by the light emitter 23 itself may influence the optical data from the optical sensor 24, and therefore it is necessary to consider the temperature of the light emitter 23 during data measurement. That is, the temperature sensor 25 is disposed close to the light emitter 23 to measure the temperature of at least the light emitter 23. The temperature sensor 25 may be disposed at any position close to the light emitter 23. The optical data may be associated with the temperature of the optical sensor 24 (particularly the light emitter 23) measured by the temperature sensor 25.

Moreover, the temperature of the light receiver 22 may also influence the measured optical data. In particular, if the light receiver 22 and the light emitter 23 are disposed in close proximity, the temperature of the light receiver 22 may greatly influence the measured optical data. That is, a temperature sensor 25 for measuring the temperature of the light receiver 22 may be installed separately, or the temperatures of both the light receiver 22 and the light emitter 23 may be measured by a single temperature sensor 25. Note that the temperature sensor 25 may be any of a negative temperature coefficient (NTC) thermistor, a thermocouple, a thermopile, or a platinum temperature sensor.

The heat radiator 26 is configured as a mechanism for radiating heat produced while the light emitter 23 is operating. In other words, the heat radiator 26 may be disposed close to the light emitter 23. In this example, the heat radiator 26 may be a heat-conducting plate, and more particularly, is disposed behind the light emitter 23 in the X-Z plane. With this arrangement, heat produced by the light emitter 23 can be radiated in the Z-axis direction. Note that in the case where a heat-conducting plate is adopted, the heat-conducting plate may contain a substance having a thermal conductivity equal to or greater than 0.20 W/(mK), more preferably 20 W/(mK). The heat radiator 26 is not limited to a heat-conducting plate, and a cooling fan, a Peltier cooling mechanism, or the like may otherwise be adopted.

(1-2) Functional Configuration Example of Measuring Device

Figure 3:
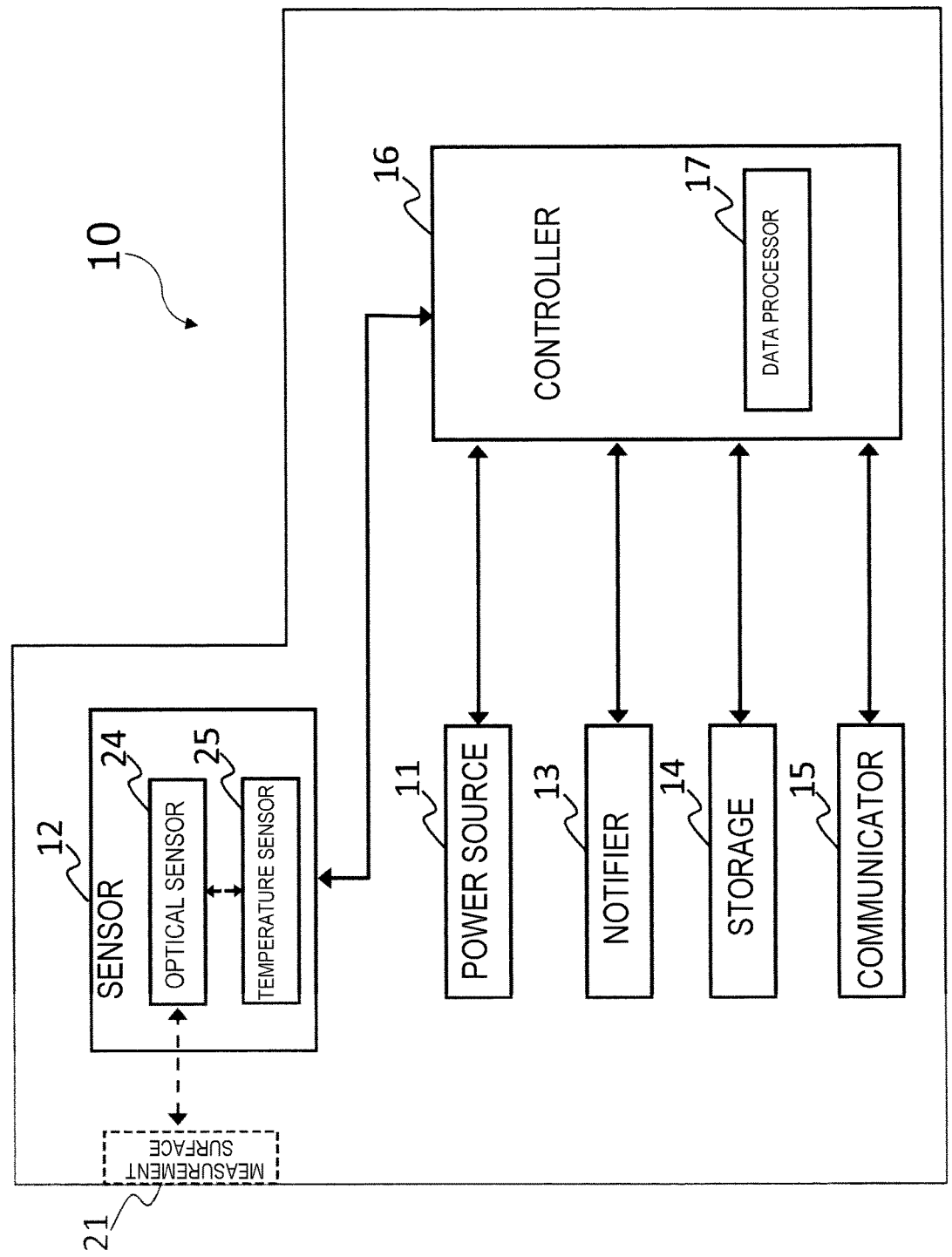
FIG. 3 is a schematic diagram illustrating a configuration example of the measuring device in FIG. 1.

FIG. 3 is a schematic diagram of a functional configuration example of the measuring device 10 for biological tissue according to the present embodiment. As illustrated in FIG. 3, the measuring device 10 according to the present configuration example includes a power source 11, a sensor 12, a notifier 13, storage 14, a communicator 15, and a controller 16. The controller 16 includes a data processor 17.

The power source 11 stores electric power and also supplies electric power to each component of the measuring device 10 on the basis of control by the controller 16. The power source 11 may be formed from a rechargeable battery such as a lithium-ion secondary cell, for example. Alternatively, the power source 11 may be formed from a primary battery such as a manganese dry cell battery or an alkaline manganese battery.

The sensor 12 acquires various information pertaining to the measuring device 10. The sensor 12 includes the optical sensor 24 and the temperature sensor 25 described above. Specifically, the optical sensor 24 emits light from the light emitter 23 to the object of measurement through the measurement surface 21 and receives reflected light from the object of measurement through the measurement surface 21 with the light receiver 22. The temperature sensor 25 is disposed close to the light emitter 23 and measures the temperature of the optical sensor 24 (particularly the light emitter 23). Otherwise, the sensor 12 is provided with an input device which includes a button, a switch or the like and which receives the input of information from the user.

The notifier 13 notifies the user of various information. For example, the notifier 13 is configured as a light-emitting device (for example, an LED) that emits light, a display device that displays information such as images and text, a sound output device that outputs sound, a vibration device that vibrates, or the like. For example, a measurement result pertaining to the object of measurement measured by the measuring device 10 may be displayed on a display device.

The storage 14 stores various information for operations by the measuring device 10. The various information includes measurement data acquired by the optical sensor 24, temperature data acquired by the temperature sensor 25, and a measurement result derived in relation to biological tissue. For example, the storage 14 includes a non-volatile storage medium such as flash memory. The storage 14 also stores programs such as firmware in addition to computer-executable instructions for causing the measuring device 10 to operate.

The communicator 15 is a communication interface capable of performing communication conforming to any given wired or wireless communication standard. For example, in the case of wireless communication, Wi-Fi®, Bluetooth®, or the like may be adopted as the communication standard. Also, in the case of wired communication, a data communication cable is connected through an external connection terminal such as Micro-USB, for example. With this arrangement, data relating to operations by the measuring device 10 is inputted/outputted with respect to external equipment.

The controller 16 functions as a computational processing device and control device, and controls overall operations inside the measuring device 10 by following various programs. The controller 16 is achieved by an electronic circuit such as a central processing unit (CPU) or a microprocessor, for example. In particular, the data processor 17 starts up the sensor 12 including the optical sensor 24 and the temperature sensor 25 to acquire data, and derives a measurement result pertaining to biological tissue on the basis of the acquired optical data and temperature.

The above describes a configuration example of the measuring device 10. Obviously, the measuring device 10 is not limited to the above configuration and may take a variety of configurations exemplified below.

The measuring device 10 for biological tissue according to the present embodiment uses the optical sensor 24, is compact enough to fit in the user's hand, and can be used casually by the user. In such a measuring device 10, the measurement accuracy of the amount of a substance in biological tissue is improved by appropriately processing optical data acquired by the optical sensor 24. Furthermore, with such a measuring device 10, a measuring mechanism using the optical sensor 24 can be applied to an inhalation device such as a smoking implement.

(1-3) Example of Operations by Measuring Device

Figure 4:
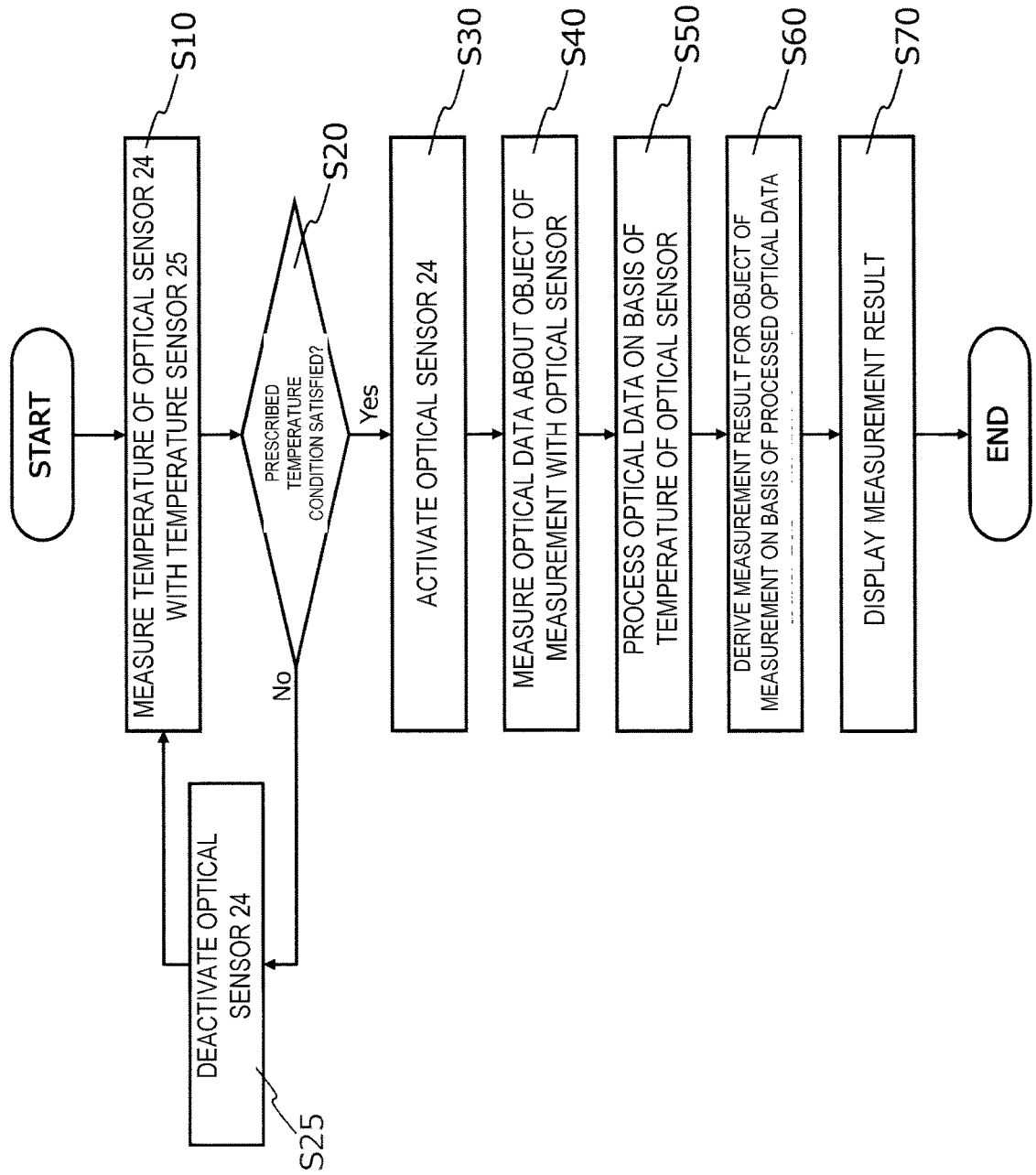
FIG. 4 is an operational flowchart illustrating a measuring method for biological tissue according to an embodiment.

FIG. 4 is a flowchart illustrating a measuring method for biological tissue according to the present embodiment, and illustrates a schematic operational flow related to operations by the measuring device 10. The following illustrates operations executed by the controller 16 as the primary entity for deriving a measurement result pertaining to biological tissue in relation to the measuring device 10, but the operations by the measuring device 10 are not limited to the following. In other words, the steps illustrated hereinafter are merely illustrative examples, any other steps may also be included, and the operational sequence of the steps is not limited except where specifically indicated in the following.

The present operational flow starts when the measuring device 10 is powered on and the measuring device 10 is started up. At this time, the temperature sensor 25 is started up. The controller 16 causes the temperature sensor 25 to measure the temperature of the optical sensor 24 (step S10). The temperature of the optical sensor 24 includes the temperature of at least the light emitter 23. In addition, the temperature of the light receiver 22 may be included.

In particular, in the case where the light receiver 22 and the light emitter 23 are disposed apart (for example, separated from each other by at least 10 mm), both the temperature of the light emitter 23 and the temperature of the light receiver 22 may be respectively acquired and used in the following process. On the other hand, in the case where the light receiver 22 and the light emitter 23 are disposed in close proximity (for example, disposed within 10 mm of each other), the temperature of the light emitter 23 and the temperature of the light receiver 22 are considered to be the same, and only the temperature of the light emitter 23 may be used.

Next, the controller 16 determines whether the measured temperature of the optical sensor 24 satisfies a prescribed temperature condition (step S20). The prescribed temperature condition may be stipulated using a prescribed temperature threshold (such as 60 degrees Celsius (° C.)), for example. The temperature condition is preset and stored in the storage 14. By providing the prescribed temperature condition, the operations of the optical sensor 24 are restricted to a desired range.

Specifically, in the case where the measured temperature of the optical sensor 24 satisfies the prescribed temperature condition by being, for example, equal to or below the prescribed temperature threshold (Yes), the measuring device 10 is considered to be capable of taking a measurement appropriately, and the optical sensor 24 is activated (step S30). On the other hand, if the temperature of the optical sensor 24 does not satisfy the prescribed temperature condition by being, for example, higher than the prescribed temperature threshold (No), the flow returns to step S10 without activating the optical sensor 24. In particular, if the optical sensor 24 is already active, the optical sensor 24 may be deactivated (step S25). Note that the entire optical sensor 24 may be subject to activation and deactivation. Alternatively, only the light emitter 23 of the optical sensor 24 or both the light receiver 22 and the light emitter 23 of the optical sensor 24 may be subject to activation and deactivation.

With this arrangement, thermal overheating of the optical sensor 24 (particularly the light emitter 23) can be prevented and the safety of the measuring device 10 can be improved. Also, the measuring device 10 can be made to operate stably under appropriate temperature conditions, and the accuracy of measurement can be improved. Furthermore, the battery of the power source 11 can also be conserved.

After step S30, the controller 16 causes the optical sensor 24 to measure optical data about the object of measurement, namely a portion of biological tissue (step S40). The measured optical data is associated with the temperature of the optical sensor 24 already measured in step S10. Note that the optical data may include a plurality of light wavelength data and the light intensity on each wavelength, for example.

Next, the data processor 17 of the controller 16 processes optical data on the basis of the already-measured temperature of the optical sensor 24 (step S50). More specifically, the data processor 17 specifies optical data by selecting the optical data for which the temperature of the optical sensor 24 substantially corresponds to a designated temperature.

Here, the designated temperature refers to a certain set value. Also, selecting the optical data for which the temperature of the optical sensor 24 substantially corresponds to the designated temperature refers to selecting the optical data associated with the temperature of the light emitter 23 from among the optical data measured in the case where the temperature of the light emitter 23 is within a fixed designated temperature zone. Furthermore, the fixed designated temperature zone refers to a zone such as 50° C.±2.0° C.

having a lower limit (48.0° C.) and an upper limit (52.0° C.) of temperature. Such information is preset and stored in the storage 14.

Note that in step S50, any means may be adopted as the configuration that selects and specifies optical data insofar as the optical data corresponding to a certain set value can be acquired. For example, the target optical data at the timing when the temperature of the optical sensor 24 corresponds to the set value may be acquired selectively in real time while the optical data is being measured in step S40. Otherwise, all of the optical data measured in step S40 may be briefly stored in the storage 14, after which only the target optical data may be selectively retained while all other optical data may be removed from the storage 14.

Next, the data processor 17 of the controller 16 derives a measurement result pertaining to the object of measurement on the basis of the optical data processed in step S50 (step S60). For example, two pieces of wavelength data included in the optical data selected as substantially corresponding to the designated temperature are used to calculate a relative ratio. Thereafter, by comparing the calculated relative ratio to a reference state value calculated and determined in advance, the state at the time of measurement may be specified with respect to a reference state.

An example of deriving a measurement result in step S60 is as follows. The following assumes that the measuring device 10 is used to measure the amount of moisture (that is, the amount of saliva) inside a person's oral cavity. In this case, the object of measurement is a person's tongue. For example, a reflection ratio of reflected light on the wavelengths 900 nm and 970 nm can be applied as a metric for measuring the amount of moisture inside a person's oral cavity. That is, among the optical data processed in step S50, data about the light intensity of reflected light on the wavelengths 900 nm and 970 nm is selectively used to calculate the relative ratio. The calculated relative ratio is the reflection ratio of reflected light on the wavelengths 900 nm and 970 nm. The light intensity of reflected light related to the wavelengths 900 nm and 970 nm can be acquired by the wavelength specifier provided in the optical sensor 24.

On the other hand, the light intensity of reflected light on the wavelengths 900 nm and 970 nm is measured in advance for a virtual dry tongue from which the saliva on a human tongue is sufficiently removed with absorbent cotton or the like, and the reflection ratio is calculated is stored in the storage 14. Thereafter, by comparing the reflection ratio measured by the measuring device 10 to the stored reflection ratio of the virtual dry tongue, the state of the tongue can be determined, such as whether the tongue is in a normal state or a dry state. Moreover, the specific amount of saliva can be calculated. In other words, by using the measuring device 10 for biological tissue according to the present embodiment, the amount of saliva inside a person's oral cavity can be measured easily. Note that the inventors have experimentally confirmed that, in one example, if the designated temperature zone is set to 45° C.±2.5° C., the reflection ratio of a tongue in the normal state is uniformly higher than the reflection ratio of the virtual dry tongue, and the relative ratio is calculated as a significant difference of approximately 1.03.

Finally, the controller 16 causes the notifier 13 to issue a notification of the measurement result derived in step S60 (step S70). For example, the user may be notified of the measurement result by displaying information such as an image on a display device. In the example of measuring the amount of saliva inside a person's oral cavity described above, the user may be notified of a specific oral health state, such as whether the tongue is in a normal state or a dry state, and the calculated amount of saliva. In addition, since the amount of saliva inside a person's oral cavity is also related to the person's bad breath, the person's bad breath level may be further calculated from the calculated amount of saliva, and the user may be notified.

When the notification of the measurement result is issued in step S70, the present operational flow ends.

In the example of operations by the measuring device 10 for biological tissue according to the present embodiment, and in the processing of the optical data in particular, optical data for which the temperature of the optical sensor 24 substantially corresponds to a designated temperature is selected. In other words, the desired optical data may simply be selected from among a plurality of optical data, and therefore the computational load imposed on the controller 16 is kept small. Also, such optical data is raw data, and therefore by using such data, the measurement result that is ultimate obtained is highly accurate compared to the case of using edited data.

(1-4) Modifications of Operations by Measuring Device (1-4-1) Modification 1

In the example of operations by the measuring device 10 described above, in step S20, a temperature condition for the operations by the measuring device 10 is set. That is, in step S20, the controller 16 determines whether the temperature of the temperature sensor 25 satisfies a prescribed temperature condition, and the process from step S30 can be executed depending on the result. Furthermore, in the present modification, an additional temperature condition for the operations by the measuring device 10 may be set, and after the optical sensor 24 is activated in step S30, the operations by the measuring device 10 may be further restricted by the controller 16.

Figure 5:
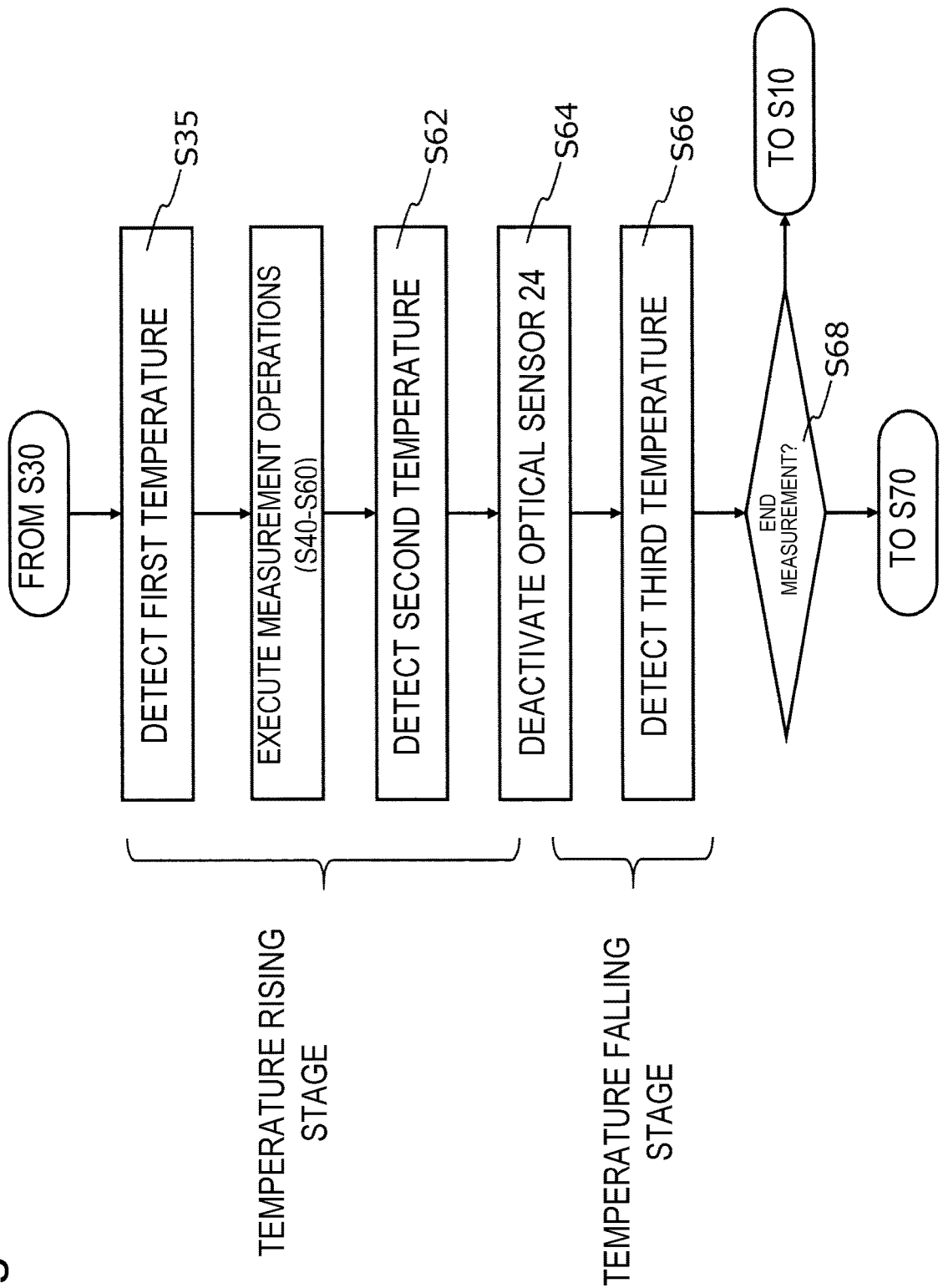
FIG. 5 is an operational flowchart illustrating a modification of the schematic operational flowchart in FIG. 4.

FIG. 5 illustrates a modification in relation to the schematic operational flow in FIG. 4, and is a schematic operational flowchart with an additional temperature condition for the operations by the measuring device 10 added between steps S30 and S70 of FIG. 4. Note that the following assumes that the notifier 13 issues a notification in response to the optical sensor 24 being activated in step S30 of FIG. 4. For example, the user is notified by turning on an LED.

If the optical sensor 24 is activated in step S30, the optical sensor 24 enters a temperature rising stage in association with the light emission by the light emitter 23. Initially, the controller 16 causes the temperature sensor 25 to detect that the optical sensor 24 has reached a first temperature (step S35). The first temperature is the lower limit of an allowed temperature range in which measuring operations are allowed to be performed. For example, the first temperature may be a temperature (for example, 20° C.) that can be reached in a few seconds after the optical sensor 24 is activated.

Alternatively, the first temperature may be the designated temperature to be used in steps S40 and S50 described above. Note that although a single designated temperature is set in the description of the operational flow in FIG. 4, the designated temperature is not limited thereto. Specifically, in the present modification, a plurality of designated temperatures may be set. If a plurality of designated temperatures are set, one designated temperature to be used during measurement is determined dynamically from among the plurality of designated temperatures. For example, a designated temperature that is higher than the ambient temperature (for example, room temperature) when the measuring device 10 is started up and also closest to the ambient temperature may be determined dynamically as the designated temperature. In particular, setting a plurality of designated temperatures is advantageous because a more appropriate set value can be selected flexibly even in the case where the measuring device 10 is used in an environment with large changes in ambient temperature. Note that the ambient temperature may be measured by the temperature sensor 25 before the optical sensor 24 is activated, or measured by a temperature sensor installed separately from the measuring device or the like.

If the temperature sensor 25 detects the first temperature in step S35, the controller 16 sequentially executes the measuring operations from steps S40 to S60 described above and derives a measurement result.

Next, the controller 16 causes the temperature sensor 25 to detect that the optical sensor 24 has reached a second temperature (step S62). The second temperature is a temperature higher than the first temperature and is the upper limit of the allowed temperature range in which measuring operations are allowed to be performed.

If the temperature sensor 25 detects the second temperature in step S62, the controller 16 determines that the temperature of the optical sensor 24 has exceeded the permissible limit for measuring operations and deactivates the optical sensor 24 (step S64). If the optical sensor 24 is deactivated, the controller 16 may additionally cause the notifier 13 to issue a notification. For example, the LED may be turned off or blinked to notify the user that the measuring device 10 has exceeded the permissible limit.

If the optical sensor 24 is deactivated in step S64, the optical sensor 24 enters a temperature falling stage. Next, the controller 16 causes the temperature sensor 25 to detect that the optical sensor 24 has fallen to a third temperature (step S66). The third temperature is a resume temperature for allowing measuring operations to be performed again, and may be same or lower than the first temperature which is the lower limit of the allowed temperature range. If the third temperature is detected, the controller 16 may additionally cause the notifier 13 to issue a notification. For example, the LED that was turned off in step S64 may be turned on again to notify the user that the measuring device 10 can resume measurement.

In step S68, the controller 16 determines whether to end the measuring operations by the measuring device 10 (step S68). For example, the determination may be made according to whether an instruction is received from the user via a button, a switch, or the like. In the case of ending measuring operations (Yes), the flow proceeds to step S70 in FIG. 3, the measurement result is displayed by the notifier 13, and thereafter the measuring operations end. On the other hand, in the case of not ending measuring operations (No), the present operational flow may return to step S30 in FIG. 3, for example.

In the present modification, by adding an additional temperature condition for the operations by the measuring device 10, thermal overheating of the optical sensor 24 (particularly the light emitter 23) can be prevented, for example, and the safety of the measuring device 10 can be improved. Also, the measuring device 10 can be made to operate stably under appropriate temperature conditions, and the accuracy of measurement can be improved. Furthermore, by deactivating the optical sensor 24 as appropriate, the battery of the power source 11 can also be conserved.

(1-4-2) Modification 2

Figure 6:
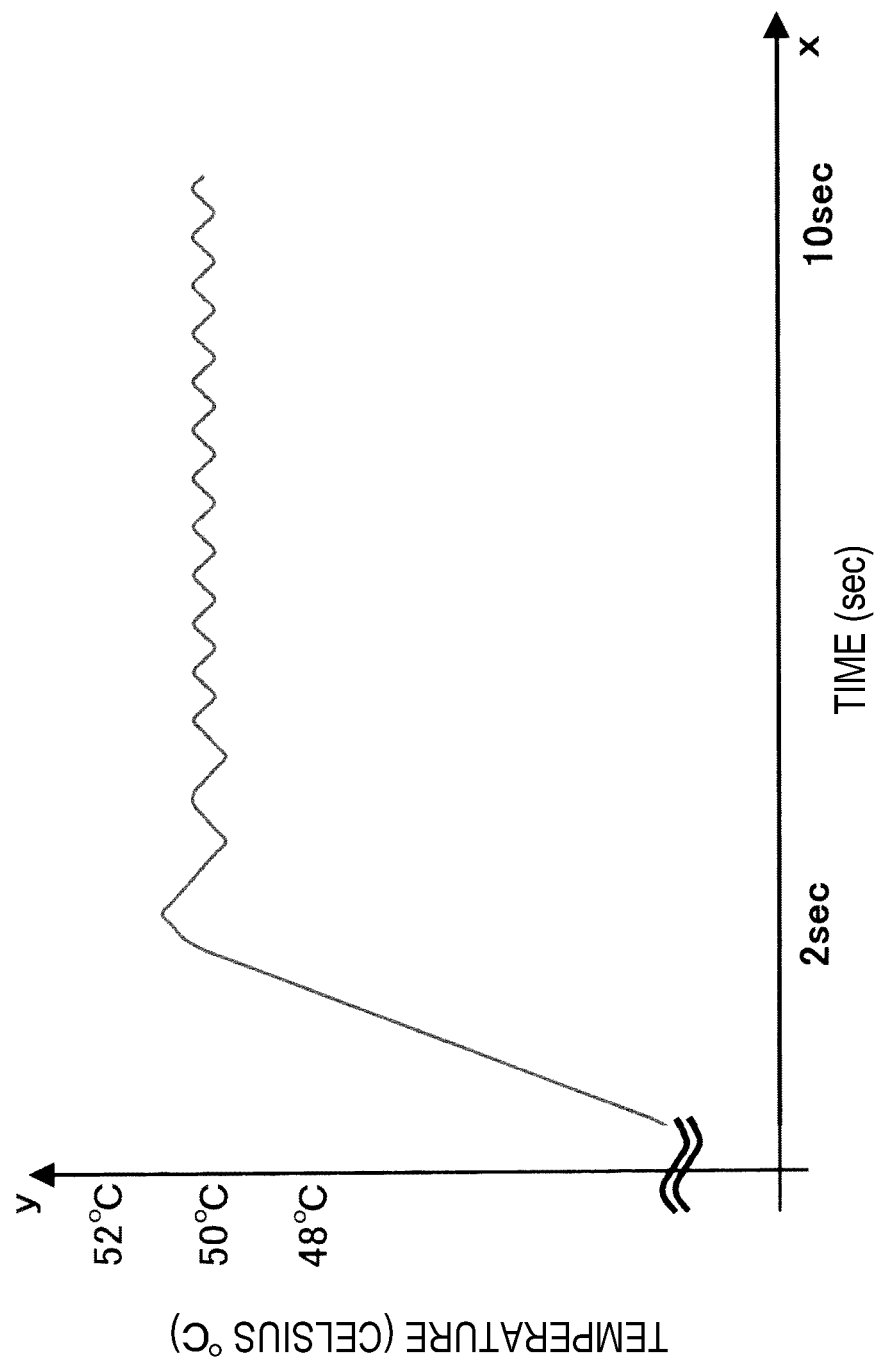
FIG. 6 is a schematic graph illustrating an example of temperature transitions in an optical sensor associated with temperature control operations.

In addition to the example of operations by the measuring device 10 described above, in the present modification, the controller 16 may also execute temperature control operations to maintain the temperature of the optical sensor 24 at the designated temperature. FIG. 6 is a schematic graph of temperature transitions in the optical sensor 24 in the case where the controller 16 executes temperature control operations. In the graph in FIG. 6, the horizontal axis (x axis) is time (sec) and the vertical axis (y axis) is the temperature (° C.) of the optical sensor 24.

In the temperature control operations, the controller 16 may take a light pulse measurement in the optical sensor 24 and perform known lock-in detection using the pulse frequency to execute a light noise process. With this arrangement, as illustrated in FIG. 6, the temperature of the optical sensor 24 can be maintained in the designated temperature zone (48° C. to 52° C.) pertaining to the designated temperature of 50° C. for approximately 8 seconds, for example.

By executing such temperature control operations, the measuring device 10 can be stabilized in a desired state. The accuracy of the measurement data can also be improved. Furthermore, the battery of the power source 11 can be conserved.

(1-4-3) Modification 3

In the example of operations by the measuring device 10 described above, in the processing of optical data in step S50, the optical data necessary to derive a measurement result is specified by selecting the optical data for which the temperature of the optical sensor 24 substantially corresponds to the designated temperature. In the present modification, instead of or in addition to the above, the optical data necessary to derive a measurement result may be specified by correcting, for each wavelength of the reflected light, the optical data acquired by the optical sensor 24 on the basis of the temperature of the optical sensor 24 acquired by the temperature sensor 25.

Figure 7:
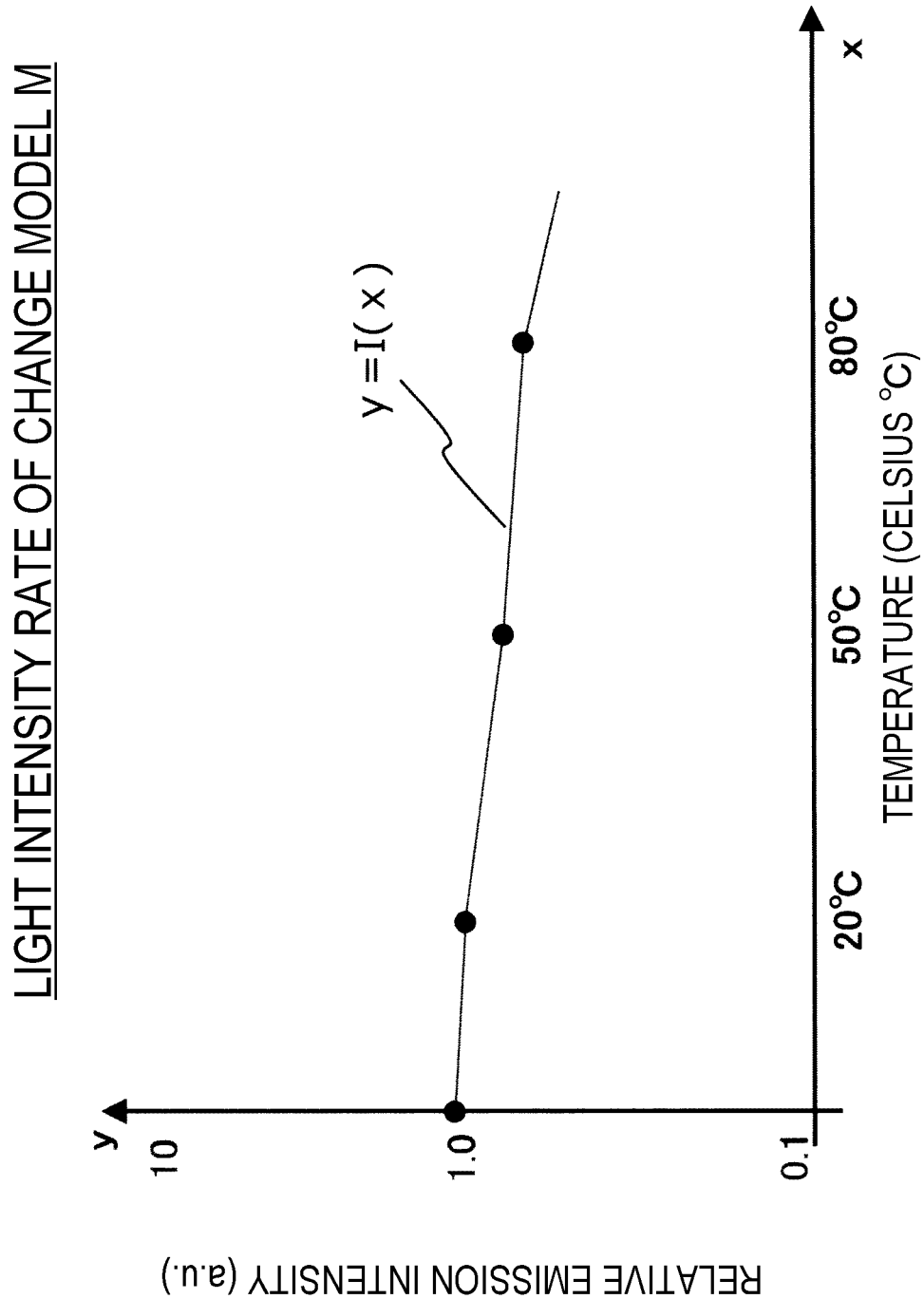
FIG. 7 is a schematic graph illustrating an example of a model of the rate of change of light intensity.

More specifically, in the present modification, a model of the rate of change of light intensity with respect to the temperature of the optical sensor 24 is defined for each wavelength in advance and stored in the storage 14. The model of the rate of change of light intensity is created on the basis of empirical data acquired through experiment. FIG. 7 illustrates an example of such a model of the rate of change of light intensity. In the graph in FIG. 7, the horizontal axis (x axis) is the temperature (° C.) of the optical sensor 24 and the vertical axis (y axis) is the relative emission intensity of the optical sensor 24. The emission intensity is a relative emission intensity in which the value for a temperature of 0° C. is normalized to 1.0.

As illustrated by the graph, by creating a regression model using the data for each of the relative emission intensities at temperatures of 20° C., 50° C., and 80° C., for example, a model $M(y=I(x))$ of the rate of change of light intensity can be created. Note that the creation of the model of the rate of change of the light intensity is not limited to the above, and various models may also be generated through machine learning using an enormous number of data points.

In the processing of the optical data in step S50, the optical data acquired by the optical sensor 24 may be corrected using the model M of the rate of change of light intensity. Specifically, if $I_\Lambda(t)$ is taken to be the rate of intensity change for each wavelength $\Lambda$ with respect to the temperature t of the optical sensor 24, a corrected light intensity $I_{c1}(\Lambda)$ corrected on the basis of the temperature of the optical sensor 24 is defined as in the following Expression 1.

$$I_{c1}(\Lambda) = I(\Lambda)/I_\Lambda(t) \qquad (1)$$

Here, $I(\Lambda)$ is the measurement value of the actual (uncorrected) light intensity for the wavelength $\Lambda$ measured by the optical sensor 24.

As described above, in the measuring operations, the optical data from the optical sensor 24 is influenced by heat produced by the operations of the light emitter 23. Furthermore, the temperature of the light receiver 22 may also influence the measured optical data. Accordingly, in the present modification, to further improve the measurement accuracy of the measuring device 10, the optical data obtained by the light receiver 22 may be corrected on the basis of not only the temperature of the light emitter 23 but also the temperature of the light receiver 22. In particular, in the case where the light receiver 22 and the light emitter 23 are disposed apart (for example, separated from each other by at least 10 mm), the optical data may be corrected on the basis of both the temperature of the light emitter 23 and the temperature of the light receiver 22.

Specifically, let $t_D$ be the temperature of the light receiver 22 and is be the temperature of the light emitter 23. Also, let $I_{AD}(t_D)$ be the rate of intensity change for each wavelength $\Lambda$ with respect to the temperature $t_D$ of the light receiver 22, and let $I_{AS}(t_S)$ be the rate of intensity change for each wavelength $\Lambda$ with respect to the temperature $t_S$ of the light emitter 23. In this case, a corrected light intensity $I_{c2}(\Lambda)$ corrected on the basis of both the temperature of the light receiver 22 and the temperature of the light emitter 23 is defined as in the following Expression 2.

$$I_{c2}(\Lambda)=1(\Lambda)/(I_{AS}(t_S) \times I_{AD}(t_D)) \quad (2)$$

By using Expression 2, a process related to the correction of the optical data in step S50 can be executed. Note that if the light receiver 22 and the light emitter 23 are disposed in close proximity, the temperature $t_D$ of the light receiver 22 may be considered the same as the temperature $t_S$ of the light emitter 23 (that is, $t_D=T_S$), and the process related to the correction of the optical data in step S50 may be executed on the basis of Expression 2.

Through experiment, the inventor discovered that if the temperature $t_D$ of the light receiver 22 and the temperature $t_S$ of the light emitter 23 are in the temperature range from approximately 15° C. to 60° C., the accuracy of the corrected light intensity is maintained through the correction of the optical data. Also, instead of the above 60° C., the upper limit of such a temperature range may be set to an operation-guaranteeing value for the light receiver 22 (a spectroscope, for example) and the light emitter 23 (an LED, for example).

By using a model of the rate of change of light intensity to correct the optical data acquired by the optical sensor 24 like in the present modification, the timing of measurement is no longer restricted by the temperature condition on the optical sensor 24. In other words, the measuring device 10 can take measurements at any timings, making the measuring device 10 even easier to use for the user. In particular, in the case where the measuring device 10 is compact and the user carries the measuring device 10, measurements can be taken with stable and consistent accuracy, without being influenced by various temperatures depending on the season or location.

Note that with regard to the processing of the optical data in step S50, the method for correcting the optical data for each wavelength of the reflected light in the present modification can be executed in combination with the method for selecting the optical data for which the temperature of the optical sensor 24 substantially corresponds to the designated temperature described above.

(2) Second Embodiment

The measuring device 10 for biological tissue according to the first embodiment described above is configured as a standalone measuring device 10. In contrast, in the second embodiment, the measuring device 10 for biological tissue is provided to an inhalation device 100. That is, the measuring device 10 for biological tissue according to the second embodiment treats oral tissue as the object of measurement that is a portion of biological tissue, and is integrated with the inhalation device 100.

In this way, the measuring device 10 is provided to the inhalation device 100 and used as a portion thereof. The inhalation device 100 according to the present embodiment is compact enough to fit in the user's hand, and can be carried and used casually by the user. Moreover, the inhalation device 100 can also be used as a measuring device 10 for oral tissue.

Note that the inhalation device 100 is a device that generates a substance to be inhaled by the user and may be an electronic tobacco product or a nebulizer, but is not limited thereto. The inhalation device 100 may also be a heated flavor inhaler or a non-heated flavor inhaler, and in particular, may include any of various inhalation devices that generate an aerosol or an aerosol with added flavor to be inhaled by the user. Moreover, the generated inhalation component may also contain a gas such as invisible vapor in addition to an aerosol.

(2-1) Functional Configuration Example of Inhalation Device (2-1-1 Configuration Example 1 of Inhalation Device)

Figure 8:
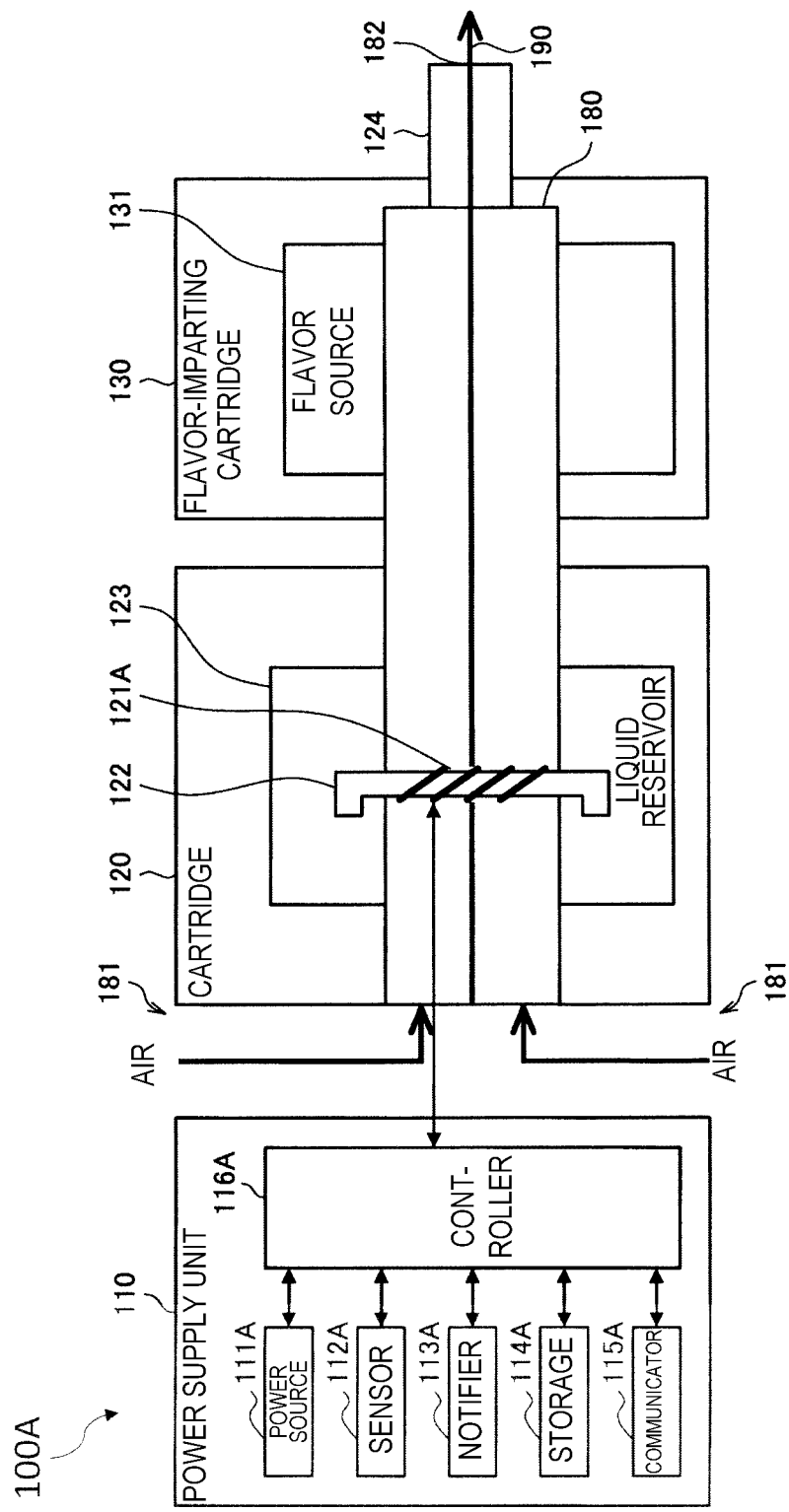
FIG. 8 is a schematic diagram illustrating a configuration example of an inhalation device according to the present embodiment.

FIG. 8 is a schematic diagram illustrating a first configuration example of an inhalation device. As illustrated in FIG. 8, an inhalation device 100A according to the present configuration example includes a power supply unit 110, a cartridge 120, and a flavor-imparting cartridge 130. The power supply unit 110 includes a power source 111A, a sensor 112A, a notifier 113A, storage 114A, a communicator 115A, and a controller 116A. The cartridge 120 includes a heater 121A, a liquid channel 122, and a liquid reservoir 123. The flavor-imparting cartridge 130 includes a flavor source 131 and a mouthpiece 124. An air channel 180 is formed in the cartridge 120 and the flavor-imparting cartridge 130.

Of the above, the power source 111A, sensor 112A, notifier 113A, storage 114A, communicator 115A, and controller 116A included in the power supply unit 110 substantially includes the configuration of each of the power source 11, sensor 12, notifier 13, storage 14, communicator 15, and controller 16 (data processor 17) included in the measuring device 10 according to the first embodiment. Hereinafter the configuration that functions as an inhalation device will be described.

The sensor 112A acquires various information pertaining to the inhalation device 100A. For example, the sensor 112A may be a pressure sensor such as a microphone condenser, a flow sensor, a temperature sensor, or the like, and acquires a value associated with inhalation by the user.

The storage 114A stores various information for operations by the inhalation device 100A. The storage 114A also stores programs such as firmware in addition to computer-executable instructions for causing the inhalation device 100A to operate.

The liquid reservoir 123 stores an aerosol source. An aerosol is generated by atomizing the aerosol source. For example, the aerosol source may be a polyhydric alcohol such as glycerin or propylene glycol and a liquid such as water. The aerosol source may also contain tobacco-derived or non-tobacco-derived flavor components. In the case where the inhalation device 100A is a medical inhaler such as a nebulizer, the aerosol source may also contain a medicine.

The aerosol source, that is, the liquid stored in the liquid reservoir 123, is channeled from the liquid reservoir 123 and held in the liquid channel 122. For example, the liquid channel 122 is a wick formed by twisting fiber materials such as glass fiber or other porous materials such as porous ceramics. In this case, the aerosol source stored in the liquid reservoir 123 is channeled by the capillary effect of the wick.

The heater 121A heats the aerosol source to atomize the aerosol source and generate an aerosol. In the example illustrated in FIG. 8, the heater 121A is configured as a coil that is wound around the liquid channel 122. When the heater 121A generates heat, the aerosol source held in the liquid channel 122 is heated and atomized, and an aerosol is generated. The heater 121A generates heat when supplied with power from the power source 111A. As an example, power may be supplied when the sensor 112A detects the user starting inhaling and/or the inputting of prescribed information. Additionally, the supply of power may be stopped when the sensor 112A detects the user finishing inhaling and/or the inputting of prescribed information.

The flavor source 131 is a component for imparting a flavor component to the aerosol. The flavor source 131 may contain tobacco-derived or non-tobacco-derived flavor components.

The air channel 180 is a channel for air to be inhaled by the user. The air channel 180 has a tubular structure with an air inflow hole 181 serving as an inlet for air into the air channel 180 and an air outflow hole 182 serving as an outlet for air from the air channel 180 on either end. Partway through the air channel 180, the liquid channel 122 is disposed on the upstream side (the side close to the air inflow hole 181) and the flavor source 131 is disposed on the downstream side (the side close to the air outflow hole 182). Air flowing in from the air inflow hole 181 in association with inhalation by the user is mixed with the aerosol generated by the heater 121A, and as indicated by the arrow 190, passes through the flavor source 131 and is transported to the air outflow hole 182. When the fluid mixture of aerosol and air passes through the flavor source 131, the flavor component contained in the flavor source 131 is imparted to the aerosol.

The mouthpiece 124 is a member that is put into the user's mouth during inhalation. The air outflow hole 182 is disposed in the mouthpiece 124. The user puts the mouthpiece 124 into the user's mouth and inhales, and can thereby draw in the fluid mixture of aerosol and air into the oral cavity.

The above describes configuration example 1 of the inhalation device 100A. Obviously, the configuration of the inhalation device 100A is not limited to the above and may take a variety of configurations exemplified below.

For example, the inhalation device 100A does not have to include the flavor-imparting cartridge 130. In this case, the mouthpiece 124 is provided on the cartridge 120.

As another example, the inhalation device 100A may also include multiple types of aerosol sources. By causing multiple types of aerosols generated from the multiple types of aerosol sources to be mixed inside the air channel 180 and inducing a chemical reaction, still other types of aerosols may be generated.

Additionally, the means for atomizing the aerosol source is not limited to heating by the heater 121A. For example, the means for atomizing the aerosol source may also be vibration atomization or induction heating.

(2-1-2 Configuration Example 2 of Inhalation Device)

Figure 9:
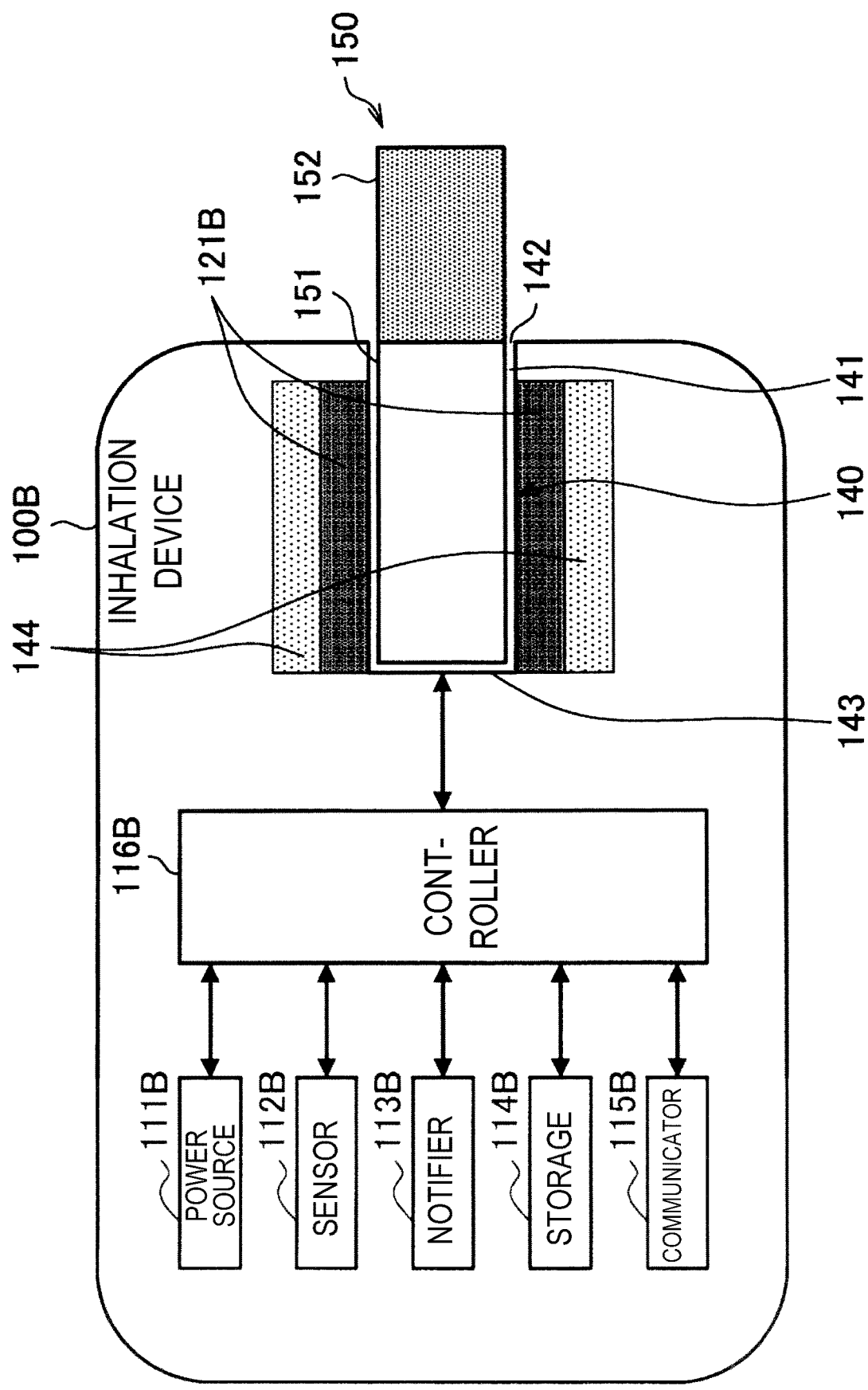
FIG. 9 is a schematic diagram illustrating another configuration example of an inhalation device.

FIG. 9 is a schematic diagram illustrating a second configuration example of an inhalation device. In an inhalation device 100B, a stick-type substrate 150 is inserted, for example, the stick-type substrate 150 including a flavor-producing substrate such as a filling which is an inhalation component source containing an aerosol source and a flavor source. Note that in the present configuration example, the aerosol source is not limited to a liquid and may also be a solid. The inserted stick-type substrate 150 is heated from the outer circumference thereof, and thereby generates a flavor-containing aerosol.

As illustrated in FIG. 9, the inhalation device 100B according to the present configuration example includes a power source 111B, a sensor 112B, a notifier 113B, storage 114B, a communicator 115B, a controller 116B, a heater 121B, a holder 140, and an insulator 144.

The power source 111B, the sensor 112B, the notifier 113B, the storage 114B, the communicator 115B, and the controller 116B each function in substantially the same way as the corresponding component included in the inhalation device 100A according to configuration example 1.

The holder 140 has an internal space 141 and holds the stick-type substrate 150 while accommodating a portion of the stick-type substrate 150 in the internal space 141. The holder 140 has an opening 142 that connects the internal space 141 to the outside and holds the stick-type substrate 150 inserted into the internal space 141 from the opening 142. For example, the holder 140 is a cylindrical body having the opening 142 and a base part 143 as a base, and demarcates a columnar internal space 141. The holder 140 also has a function of demarcating a channel for air to be supplied to the stick-type substrate 150. An air inflow hole serving as an inlet for air into the channel is disposed in the base part 143, for example. On the other hand, an air outflow hole serving as an outlet for air from the channel is the opening 142.

The stick-type substrate 150 includes a substrate part 151 and an inhaling part 152. The substrate part 151 includes an aerosol source. In the state with the stick-type substrate 150 held by the holder 140, at least a portion of the substrate part 151 is accommodated in the internal space 141, and at least a portion of the inhaling part 152 projects out from the opening 142. Additionally, if the user puts the inhaling part 152 projecting out from the opening 142 into the user's mouth and inhales, air flows into the internal space 141 from an air inflow hole not illustrated and arrives inside the user's mouth together with an aerosol produced from the substrate part 151.

The heater 121B has a configuration similar to the heater 121A according to configuration example 1. However, in the example illustrated in FIG. 9, the heater 121B is configured in a film form and is disposed to cover the outer circumference of the holder 140. Additionally, when the heater 121B generates heat, the substrate part 151 of the stick-type substrate 150 is heated from the outer circumference, and an aerosol is generated.

The insulator 144 prevents heat transfer from the heater 121B to other components. For example, the insulator 144 is formed from a vacuum insulation material, an aerogel insulation material, or the like.

The above describes configuration example 2 of the inhalation device 100B. Obviously, the inhalation device 100B is not limited to the above configuration and may take a variety of configurations exemplified below.

As an example, the heater 121B may be configured in a blade form and may be disposed to project into the internal space 141 from the base part 143 of the holder 140. In this case, the heater 121B in the blade form is inserted into the substrate part 151 of the stick-type substrate 150 and heats the substrate part 151 of the stick-type substrate 150 from the inside. As another example, the heater 121B may be disposed to cover the base part 143 of the holder 140. Moreover, the heater 121B may also be configured as a combination of two or more of a first heating part that covers the outer circumference of the holder 140, a blade-shaped second heating part, and a third heating part that covers the base part 143 of the holder 140.

In another example, the holder 140 may also include an opening—closing mechanism such as a hinge that opens and closes a portion of a shell that forms the internal space 141. Additionally, by opening and closing the shell, the holder 140 may grip the stick-type substrate 150 inserted into the internal space 141. In this case, the heater 121B may be provided on the gripping part of the holder 140 and heat the stick-type substrate 150 while pressure is applied.

Additionally, the means for atomizing the aerosol source is not limited to heating by the heater 121B. For example, the means for atomizing the aerosol source may also be induction heating.

Also, the inhalation device 100B may further include the heater 121A, the liquid channel 122, the liquid reservoir 123, and the air channel 180 according to configuration example 1, and the air outflow hole 182 of the air channel 180 may double as an air inflow hole into the internal space 141. In this case, the fluid mixture of air and an aerosol generated by the heater 121A flows into the internal space 141, is further mixed with an aerosol generated by the heater 121B, and arrives inside the user's oral cavity.

(2-2 Exterior Example of Inhalation Device)

Figure 10:
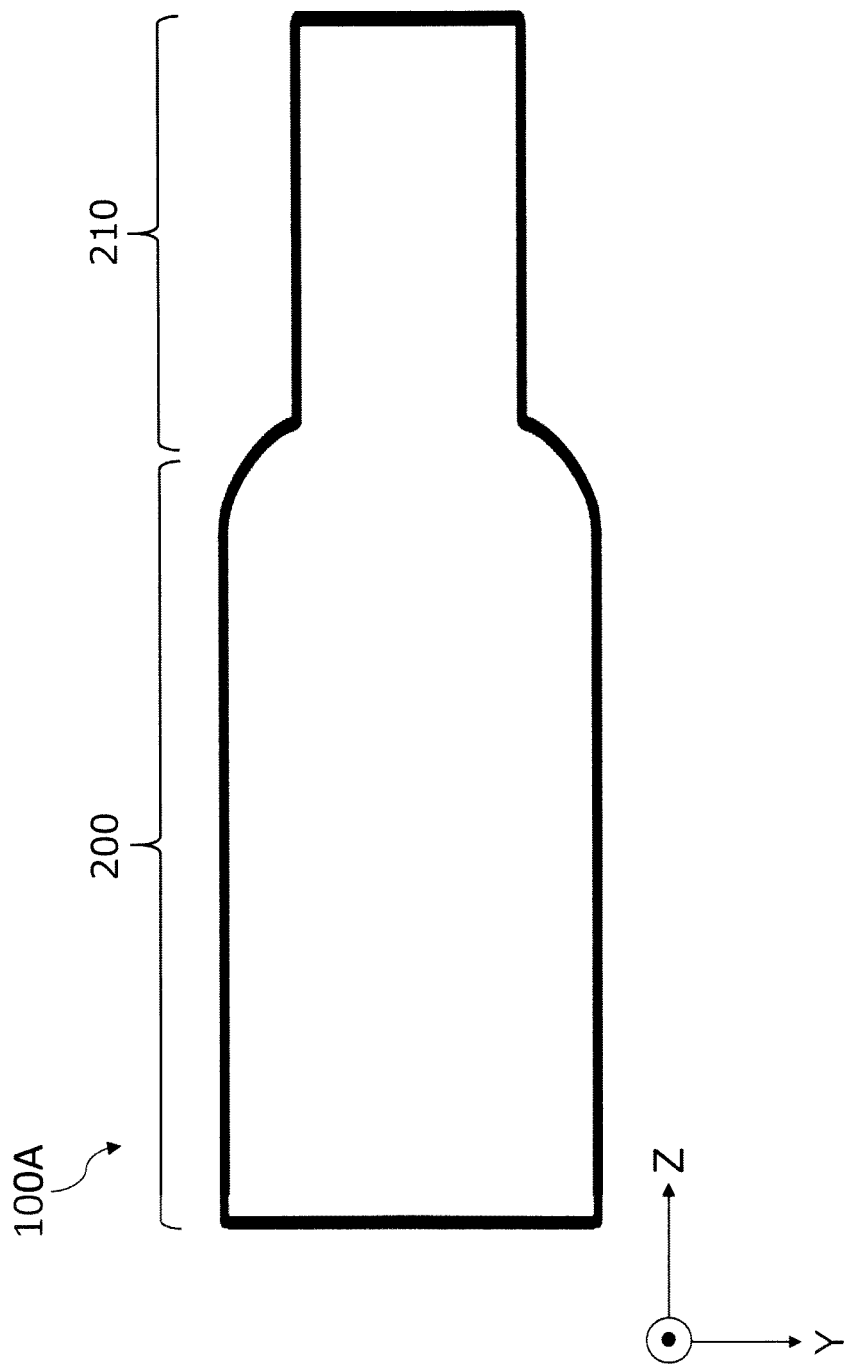
FIG. 10 is a schematic diagram illustrating an exterior view of the inhalation device in FIG. 8.

FIG. 10 is a schematic diagram illustrating a schematic exterior of an inhalation device according to the present embodiment. In the present embodiment, the inhalation device 100 is provided with the measuring device 10 for biological tissue. The following description takes the inhalation device 100A according to configuration example 1 illustrated in FIG. 8 above as an example, but is not limited thereto and also applies to the inhalation device 100B according to configuration example 2 illustrated in FIG. 9.

In the inhalation device 100A, the power supply unit 110, the cartridge 120, the flavor-imparting cartridge 130, and the mouthpiece illustrated in FIG. 8 are assembled to form the outermost housing of the inhalation device 100A. The housing of the inhalation device 100A includes a holding portion 200 and an inhaling portion 210. The user, while holding the holding portion 200 in one hand, puts the inhaling portion 210 into the user's mouth and inhales from the Z-axis direction, and thereby can draw a fluid mixture of aerosol and air into the oral cavity.

(2-3) Configuration Example of Measuring Device Provided to Inhalation Device

Figure 11:
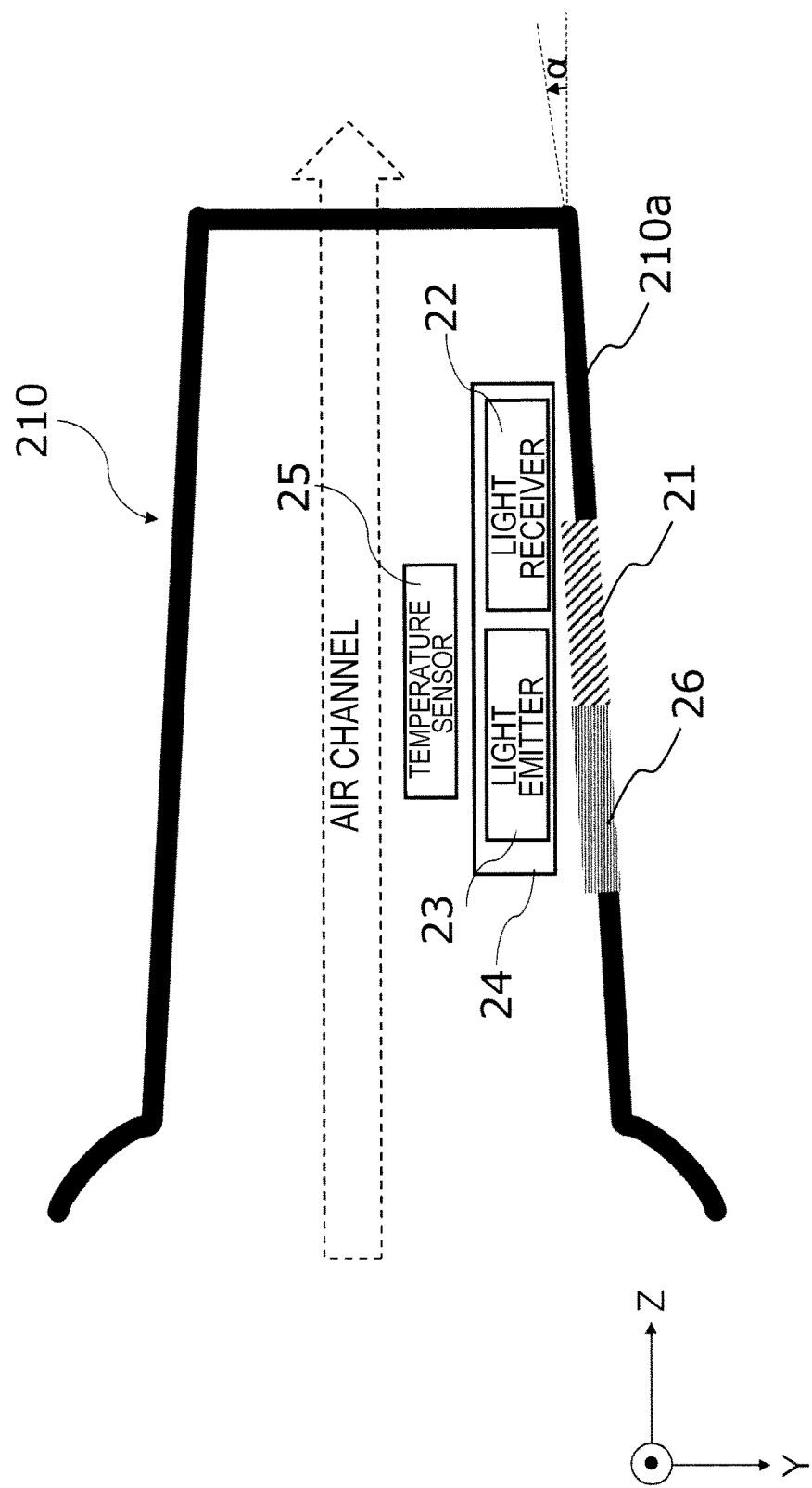
FIG. 11 is a schematic diagram illustrating an arrangement example of elements in the inhalation device in FIG. 10.
Figure 12:
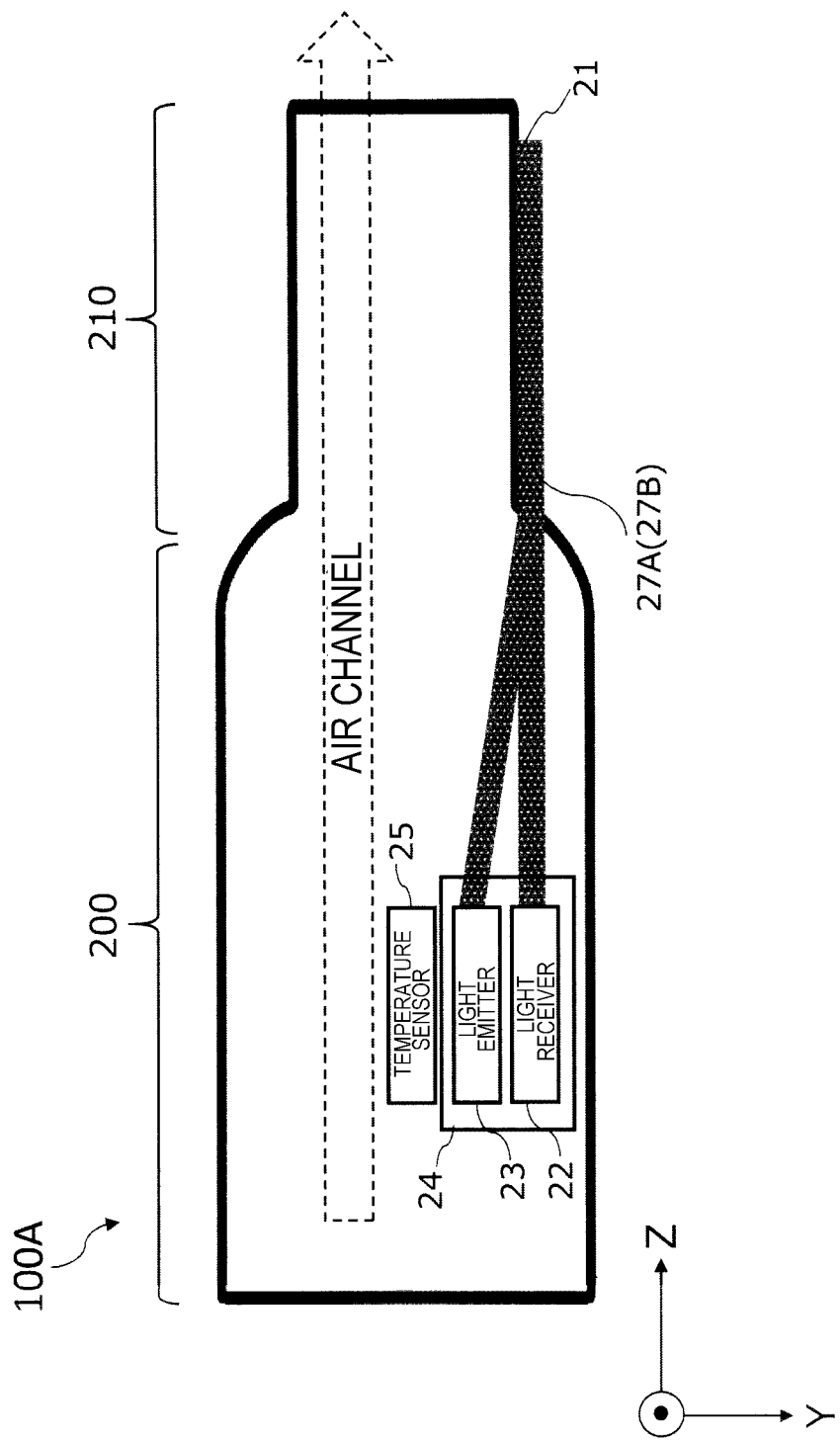
FIG. 12 is a schematic diagram illustrating another arrangement example of elements in the inhalation device in FIG. 10.

Hereinafter, the measuring device 10 provided to the inhalation device 100A will be described. Anticipated examples of measuring device 10 include a proximity type in which the optical sensor 24 and the measurement surface 21 are disposed in close proximity and a separated type in which the optical sensor 24 and the measurement surface 21 are disposed apart. FIG. 11 is an example of the proximity type and is an enlarged schematic view of the inhaling portion 210. FIG. 12 is an example of the separated type. For the most part, FIGS. 11 and 12 schematically illustrate the positional relationship between the optical sensor 24 (light receiver 22 and light emitter 23) and the measurement surface 21.

(2-3-1) Proximity-Type Arrangement Example 1

As illustrated in FIG. 11, the measurement surface 21 and the heat radiator 26 are provided on the surface of the inhaling portion 210 of the inhalation device 100A, while the optical sensor 24 and the temperature sensor 25 are disposed inside the inhaling portion 210. More specifically, the measurement surface 21 and the heat radiator 26 are provided on a lateral surface 210a of the inhaling portion 210, and the optical sensor 24 including the light receiver 22 and the light emitter 23 is disposed close to the measurement surface 21. The light receiver 22 and the light emitter 23 are disposed in parallel with the Z axis in the order of the light emitter 23 and the light receiver 22 in the +Z direction. Also, the elements of the light receiver 22 and the light emitter 23 are pointed in the +Y direction. In addition, the temperature sensor 25 is disposed close to the optical sensor 24 (particularly the light emitter 23).

The measurement surface 21 may be provided with a measurement window to be touched by the object of measurement, namely oral tissue. The measurement window is highly safe to biological tissue and may be formed using an optically transparent material. For example, acrylic resin, glass, and the like may be used, but the material is not limited thereto. Moreover, the measurement window may be shaped into a film, a plate, or the like. With this arrangement, direct contact between the optical element and biological tissue can be prevented, thereby improving the robustness of the optical sensor 24 and also improving user feel.

Note that the area of the measurement window (that is, the area of the measurement surface 21 put into contact with the object of measurement) may be 300 mm$^2$ or less, for example. Also, the measurement surface 21 is provided on the inhaling portion 210 and therefore the object of measurement may be oral tissue, but is not necessarily limited thereto. In other words, besides oral tissue such as the tongue and lower lip, the object of measurement may be applied broadly to body surface skin and the like.

The heat radiator 26 is disposed beside the measurement surface 21 on the lateral surface 210a. The heat radiator 26 may be disposed adjacent to the light emitter 23 to release heat produced by the optical sensor 24, particularly the light emitter 23, to the outside of the inhaling portion 210. The heat radiator 26 may be a heat-conducting plate, and may also be configured as a portion of the measurement surface 21. With this arrangement, released heat can be conducted to the object of measurement, namely oral tissue, to promote saliva secretion.

Also, as illustrated in the drawing, the lateral surface 210a of the inhaling portion 210 may form an inclined surface (or a tapered surface) inclined by an angle α toward the light receiver 22 with respect to the Z direction. As a result, the inhaling portion 210 has a shape that is tapered in the +Z direction. With this configuration, the angle of incidence on the light receiver 22 can be reduced and the light reception sensitivity can be improved compared to the case where an inclined surface is not provided. Note that the angle α may be adjusted in the range from 0° to 15°. More preferably, the angle α may be adjusted in the range from 1° to 5° (for example, 2°).

The measurement surface 21 may be disposed on the lateral surface 210a of the inhaling portion 210, at a position between the light receiver 22 and the light emitter 23 from the tip of the inhaling portion 210. With this arrangement, the light receiver 22 can be configured to receive light that is radiated from the light emitter 23 and reflected from the object of measurement through the measurement surface 21. The distance between the light receiver 22 and the light emitter 23 may be set from 3 mm to 20 mm. More preferably, the distance may be adjusted in the range from 5 mm to 15 mm. The distance between the light emitter 23 and the measurement surface 21 may also be set to 20 mm, more preferably adjusted to be less than or equal to 10 mm.

The temperature sensor 25 may be disposed near the light emitter 23, at a position between the optical sensor 24 and the air channel (dashed-line arrow) provided in the inhalation device 100A. When an aerosol obtained by heating and atomizing an aerosol source passes through the air channel inside the inhaling portion 210 as a fluid mixed with air, the heat of the aerosol is also thought to induce variation in the temperature of the optical sensor 24. Accordingly, a distance between the optical sensor 24 and the air channel may be secured, and the temperature sensor 25 may also be disposed in between.

In the proximity-type arrangement example, the sensor 12 including the optical sensor 24 and the temperature sensor 25 is disposed inside the inhaling portion 210 of the inhalation device 100A. Otherwise, other elements such as the controller 16 (not illustrated) are disposed inside the holding portion 200 of the inhalation device 100A. The sensor 12 and the controller 16 are electrically connected by a wire inside the inhalation device 100A.

In this way, according to the proximity-type arrangement example, the measurement surface 21 and the optical sensor 24 (light receiver 22 and light emitter 23) are disposed in close proximity, while the heat radiator 26 and the temperature sensor 25 are also disposed in close proximity inside the inhaling portion 210. With this arrangement, the influence of heat produced by the optical sensor 24 can be avoided, and the measuring device 10 can be provided even to a compact device like the inhalation device 100A.

(2-3-2) Separated-Type Arrangement Example 2

As illustrated in FIG. 12, the optical sensor 24 and the temperature sensor 25 are disposed inside the holding portion 200 of the inhalation device 100A (note that the heat radiator 26 is not illustrated). Also, the measurement surface 21 is provided in the inhaling portion 210 of the inhalation device 100A. Additionally, the light receiver 22 and the light emitter 23 are joined to the measurement surface 21 through two optical fibers 27 (27A, 27B), respectively. In other words, in the separated-type arrangement example, by applying the optical fibers 27, the light receiver 22 and the light emitter 23 inside the holding portion 200 can be separated from the measurement surface 21 inside the inhaling portion 210.

Also, the separated-type arrangement example is advantageous in that by applying the optical fibers 27, the measurement surface 21 provided on the inhaling portion 210 side can be narrowed. Note that the optical fibers 27 may be, but are not limited to, quartz fibers. Quartz fibers are known to be implemented with a diameter approximately from 200 μm to 600 μm.

Figure 13:
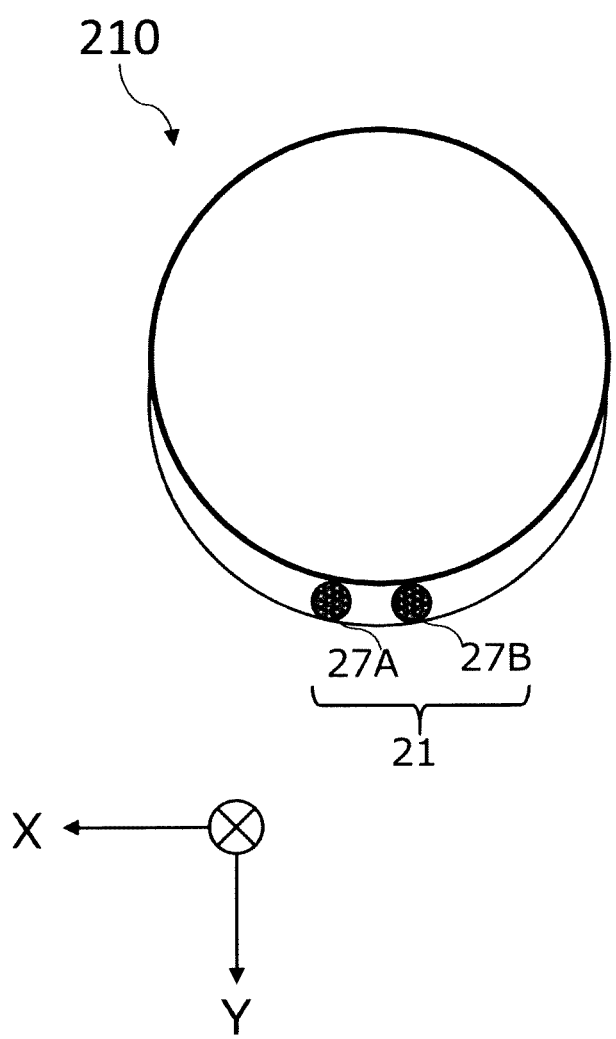
FIG. 13 is a schematic diagram illustrating another arrangement example of elements in the inhalation device in FIG. 10.
Figure 14:
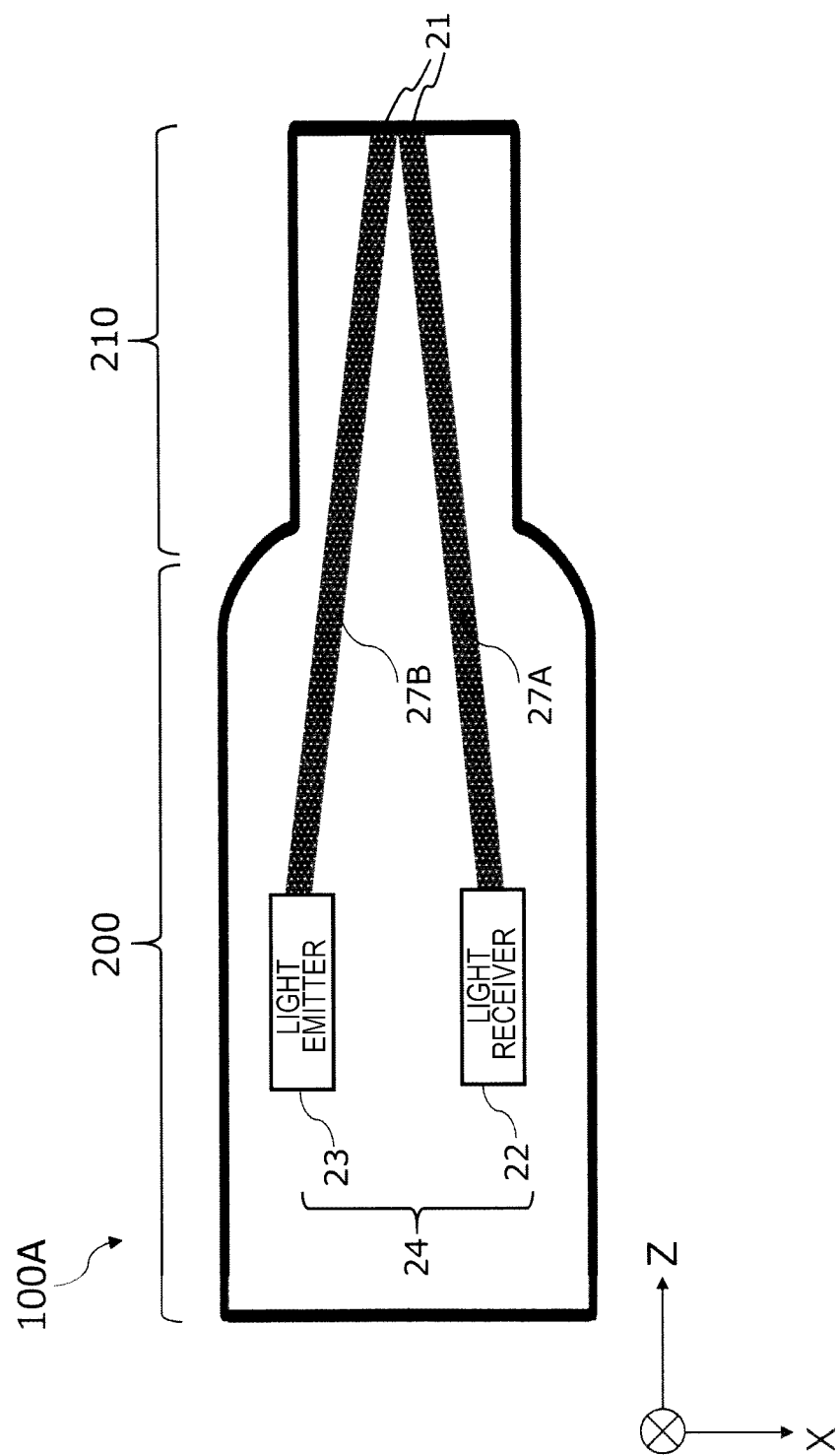
FIG. 14 is a schematic diagram illustrating another arrangement example of elements in the inhalation device in FIG. 10.

FIGS. 13 and 14 will be additionally referenced to describe the positional relationship between the optical sensor 24 (light receiver 22 and light emitter 23) and the measurement surface 21 in further detail. FIG. 13 is a plan view schematically illustrating the inhaling portion 210 of the inhalation device 100A illustrated in FIG. 12 from the Z-axis direction, and FIG. 14 is a plan view schematically illustrating the Y-Z plane of the inhalation device 100A.

Herein, two optical fibers 27A and 27B are used. Furthermore, as illustrated in FIG. 13, the end faces of the two optical fibers 27A and 27B form the measurement surface 21. The distance between the end faces of the optical fibers 27A and 27B may be set from 0 μm to 20 mm. In particular, in the case of measuring a substance on the surface of biological tissue such as an oral surface, the distance between the end faces of the optical fibers 27A and 27B may be adjusted in the range from 0 μm to 3 mm. Note that if the distance between the end faces of the optical fibers 27A and 27B is 0, the end faces of the optical fibers 27A and 27B make contact each other in some cases. In this way, by bring the end faces of the optical fibers 27A and 27B in proximity or contact with each other as the measurement surface 21, the accuracy of the measurement result can be improved.

Also, as illustrated in FIG. 14, the two optical fibers 27A and 27B may be disposed to face each other at a predetermined angle with respect to the Z-axis direction. That is, the two optical fibers 27A and 27B may be disposed such that the distance in between decreases proceeding from the optical sensor 24 (light receiver 22 and light emitter 23) toward the end faces of the optical fibers 27A and 27B. The predetermined angle may be set to 10° or less, for example. Also, the end faces of the fibers are normally at 90° with respect to the axial direction of the fibers, but the end faces may also be inclined from 80° to 90° such that the inclined surfaces face each other. With this arrangement, the light receiver 22 can receive reflected light more effectively.

Note that although two optical fibers are applied herein, a single optical fiber 27 that can be split two ways may be used instead. In this case, the measurement surface 21 side of the optical fiber 27 has one end face while the opposite side is split two ways and joined to the light receiver 22 and the light emitter 23, respectively.

Moreover, similarly to the illustration of the proximity-type arrangement, the temperature sensor 25 may be disposed near the light emitter 23, at a position between the optical sensor 24 and the air channel (dashed-line arrow) provided in the inhalation device 100A. When an aerosol obtained by heating and atomizing an aerosol source passes through the air channel inside the inhaling portion 210 as a fluid mixed with air, the heat of the aerosol is also thought to induce variation in the temperature of the optical sensor 24. Accordingly, a distance between the optical sensor 24 and the air channel may be secured, and the temperature sensor 25 may be disposed in between.

In this way, in the separated-type arrangement example, the light receiver 22 and the light emitter 23 inside the holding portion 200 are separated from the measurement surface 21 inside the inhaling portion 210 through the optical fibers 27. With this arrangement, the inhaling portion 210 in particular can be made more compact, and the measuring device 10 can be provided even to a compact device like the inhalation device 100A.

(2-4) Example of Operations by Measuring Device Provided to Inhalation Device

An example of operations by the inhalation device is as described in the first embodiment. In addition, in the present embodiment, data while the user is using the inhalation device may be applied to measuring operations.

For example, when the user holds the inhaling portion 210 in his/her mouth during inhaling operations, the lower lip is assumed to be contacting the measurement surface 21. That is, during inhaling operations, light from the light emitter 23 is reflected to the light receiver 22 by the lower lip. Utilizing this arrangement, the controller 16 may be controlled to execute the measuring operations (steps S40 to S60 in FIG. 4) only if the intensity of light (particularly, the quantity of light) received by the light receiver 22 is equal to or greater than a prescribed threshold value, for example.

Otherwise, various information (such as a puff count, a puff operation duration, and a number of consumed capsules, for example) pertaining to inhaling operations by the user may be utilized as or associated with a measurement result for the inhalation device.

(3) Third Embodiment

The measuring device 10 for biological tissue according to the first embodiment is configured as a standalone measuring device 10. Also, in the second embodiment, the measuring device 10 for biological tissue is provided to the inhalation device 100 and integrated with the inhalation device 100. In contrast, in the third embodiment, the measuring device 10 for biological tissue is configured to be removably attached to the inhalation device 100. The following description takes the inhalation device 100A according to configuration example 1 illustrated in FIG. 8 above as an example, but is not limited thereto.

In the present embodiment, for example, a mechanism may be provided such that the measuring device 10, which may also operate in a standalone manner, can be mechanically attached to the inhalation device 100A. With this configuration, when the user uses the inhalation device 100, a measurement may also be taken by the measuring device 10.

As an alternative configuration, the measuring device 10 may be electrically connected to the inhalation device 100A in accordance with the measuring device 10 being attached to the inhalation device 100A. For example, power may be fed from the power source 111A of the inhalation device 100 to the measuring device 10 to activate the sensor 12 and the controller 16. In this case, various programs and/or settings information stored in the storage 114A of the inhalation device 100A may be configured to be usable by the measuring device 10. Additionally, a notification of a measurement result may be issued by the notifier 113A of the inhalation device 100A.

Figure 15:
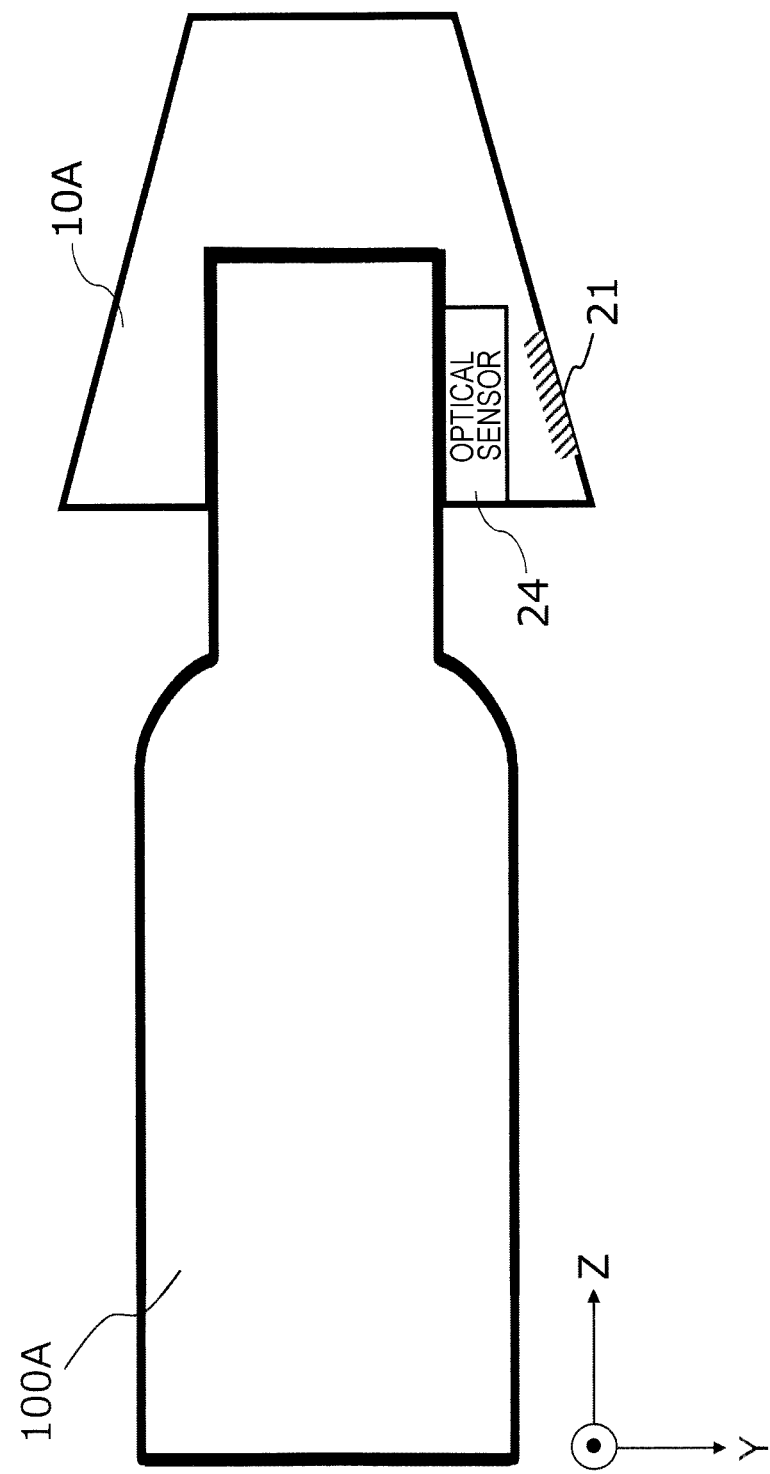
FIG. 15 is a schematic diagram illustrating an example of attaching a measuring device to the inhalation device in FIG. 8.
Figure 16:
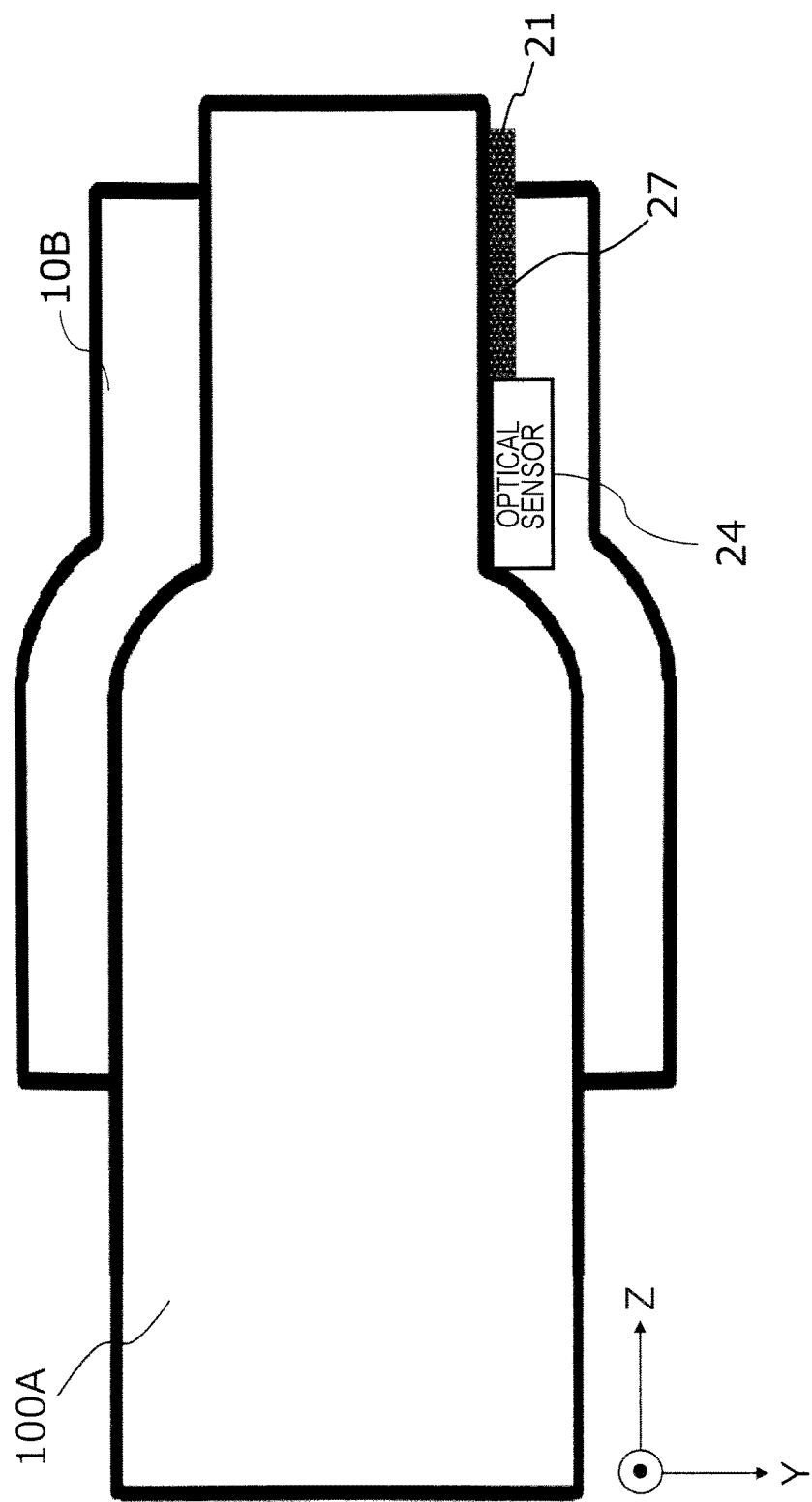
FIG. 16 is a schematic diagram illustrating another example of attaching a measuring device to the inhalation device in FIG. 8.

The measuring device 10 for biological tissue according to the present embodiment is provided with at least the sensor 12 and the measurer 20. FIGS. 15 and 16 are diagrams schematically illustrating a state in which such a measuring device 10 is attached to the inhalation device 100A.

A measuring device 10A in FIG. 15 is an example of a cap-type device that is attachable to the tip of the inhaling portion 210 of the inhalation device 100A. The cap-type measuring device 10A may be configured as an inhalation device 10A of the proximity type described in the second embodiment, for example. Specifically, as illustrated in the diagram, the measurement surface 21 is included on a tapered surface, and the optical sensor 24 is disposed close to the measurement surface. The optical sensor 24 may also be provided on an inner wall of the measuring device 10A. Note that the positional relationship between the measurement surface 21 and the optical sensor 24 is as described in the second embodiment. (The temperature sensor 25 and the heat radiator 26 are omitted from illustrated here.)

A measuring device 10B in FIG. 16 is an example of a case-type device that is attachable by being penetrated by the tip of the inhaling portion 210 of the inhalation device 100A. The case-type measuring device 10B may be configured as an inhalation device 10A of the separated type described in the second embodiment, for example. The optical sensor 24 and the optical fibers 27 may be provided on an inner wall of the measuring device 10B. Additionally, as illustrated in the diagram, the optical fibers 27 running from the optical sensor 24 may be positioned to form the measurement surface 21 adjoining the inhaling portion 210 of the inhalation device 100A when the measuring device 10B is attached. (Like FIG. 15, the temperature sensor 25 and the heat radiator 26 are omitted from illustrated here.)

The measuring devices 10A and 10B for biological tissue according to the present embodiment can be freely and removably attached to the inhalation device 100A. The inhalation device 100A may also be operable while the measuring device 10A or 10B is attached to the inhalation device 100A. In this way, the measuring devices 10A and 10B are sufficiently compact devices, and the user can casually use the measuring device 10 together with the inhalation device 100A.

(4) Other Embodiments

In the above description, a measuring device, an inhalation device, and a method according to several embodiments are described with reference to the drawings. It is understood that the present disclosure may also be carried out as a program that, when executed by a processor, causes the processor to execute a method causing the measuring device or the inhalation device to operate, or may be carried out as a computer-readable storage medium storing the program.

The foregoing describes embodiments of the present disclosure along with modifications and applications thereof, but it should be understood that the above examples are merely for illustrative purposes and do not limit the scope of the present disclosure. It should be understood that changes, additions, improvements, and the like can be made to the embodiments without departing from the gist and scope of the present disclosure. The scope of the present disclosure should not be limited by any of the embodiments described above, but should be defined only by the claims and their equivalents.

REFERENCE SIGNS LIST 10, 10A, 10B measuring device
17 data processor
20 measurer
21 measurement surface
22 light receiver
23 light emitter
24 optical sensor
25 temperature sensor
26 heat radiator
27 (27A, 27B) optical fiber
30 main body
100 (100A, 100B) inhalation device
110 power supply unit
11, 111A, 111B power source
12, 112A, 112B sensor
13, 113A, 113B notifier
14, 114A, 114B storage
15, 115A, 115B communicator
16, 116A, 116B controller
120 cartridge
121A, 121B heater
122 liquid channel
123 liquid reservoir
124 mouthpiece
130 flavor-imparting cartridge
131 flavor source
140 holder
141 internal space
142 opening
143 base
144 insulator 150 stick-type substrate
151 substrate part
152 inhaling part
180 air channel
181 air inflow hole
182 air outflow hole
200 holding portion
210 inhaling portion

The invention claimed is:

1. A measuring device for biological tissue, the measuring device comprising:
an optical sensor that measures optical data about an object of measurement through a measurement surface in contact with the object of measurement by irradiating the object of measurement with light from a light emitter and causing a light receiver to receive reflected light that is reflected from the object of measurement, the object of measurement being a portion of the biological tissue;
a temperature sensor that measures a temperature of the optical sensor; and
a data processor that processes the optical data on a basis of the temperature of the optical sensor and derives a measurement result pertaining to the object of measurement on a basis of the processed optical data,
wherein the processing of the optical data by the data processor includes selecting the optical data which is measured in the state that the temperature of the optical sensor indicates a designated temperature.

2. The measuring device according to claim 1, wherein the designated temperature is determined dynamically on a basis of an ambient temperature when the measuring device is started up.

3. The measuring device according to claim 1, wherein the processing of the optical data by the data processor includes correcting the optical data for each wavelength of the reflected light on a basis of the temperature of the optical sensor.

4. The measuring device according to claim 3, wherein a model of a rate of change of light intensity with respect to the temperature of the optical sensor is defined for each wavelength in advance and stored in storage, and the optical data is corrected by using the model.

5. The measuring device according to claim 1, wherein the light emitter is activated if the temperature of the optical sensor is equal to or lower than a prescribed threshold value, and
the light emitter is deactivated if the temperature of the optical sensor is higher than the prescribed threshold value.

6. The measuring device according to claim 1, wherein the measurement surface comprises an optically transparent window.

7. The measuring device according to claim 6, wherein the measurement surface is disposed on an inclined surface at a position between the light receiver and the light emitter.

8. The measuring device according to claim 7, wherein an angle of inclination of the inclined surface is less than or equal to 15 degrees.

9. The measuring device according to claim 1, wherein the light emitter and the light receiver are joined to the measurement surface through an optical fiber.

10. The measuring device according to claim 9, wherein the optical fiber comprises a first fiber joining the light emitter and the measurement surface and a second fiber joining the light receiver and the measurement surface, and
a distance between an end of the first fiber on the measurement surface side and an end of the second fiber on the measurement surface side is within a range from 0 mm to 3 mm.

11. The measuring device according to claim 1, wherein the measuring device is provided to an inhalation device and is integrated with the inhalation device.

12. The measuring device according to claim 11, wherein the temperature sensor is disposed between an air channel provided in the inhalation device and the optical sensor.

13. The measuring device according to claim 1, wherein the measuring device is removably attached to an inhalation device.

14. The measuring device according to claim 11, wherein the object of measurement is oral tissue.

15. An inhalation device comprising the measuring device according to claim 1.

16. The measuring device according to claim 12, wherein the object of measurement is oral tissue.

17. A measuring method for biological tissue, the measuring method comprising:
a step of a temperature sensor measuring a temperature of an optical sensor;
a step of the optical sensor measuring optical data, the step including
irradiating an object of measurement with light and receiving reflected light that is reflected from the object of measurement through a measurement surface in contact with the object of measurement, the object of measurement being a portion of the biological tissue;
a step for processing the optical data on a basis of the temperature of the optical sensor, including selecting the optical data which is measured in the state that the temperature of the optical sensor indicates a designated temperature; and
a step for deriving a measurement result pertaining to the object of measurement on a basis of the processed optical data.

18. The measuring method according to claim 17, wherein the step for processing the optical data includes correcting the optical data for each wavelength of the reflected light on a basis of the temperature of the optical sensor.

* * * * *